(12) United States Patent
Wrenn et al.

(10) Patent No.: US 10,688,040 B2
(45) Date of Patent: *Jun. 23, 2020

(54) ENCAPSULATION OF MICROBUBBLES WITHIN THE AQUEOUS CORE OF MICROCAPSULES

(71) Applicants: Steven P. Wrenn, Swarthmore, PA (US); Stephen Dicker, Philadelphia, PA (US)

(72) Inventors: Steven P. Wrenn, Swarthmore, PA (US); Stephen Dicker, Philadelphia, PA (US)

(73) Assignee: Drexel University, Philadelphia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/291,774

(22) Filed: Mar. 4, 2019

(65) Prior Publication Data

US 2019/0262260 A1    Aug. 29, 2019

Related U.S. Application Data

(63) Continuation of application No. 13/264,335, filed as application No. PCT/US2010/031772 on Apr. 20, 2010, now Pat. No. 10,258,563.

(60) Provisional application No. 61/170,830, filed on Apr. 20, 2009.

(51) Int. Cl.
    *A61K 9/00* (2006.01)

(52) U.S. Cl.
    CPC .................. *A61K 9/0009* (2013.01)

(58) Field of Classification Search
    CPC .................. A61K 9/0009; A61K 47/6925
    See application file for complete search history.

(56) References Cited

U.S. PATENT DOCUMENTS

| | | | |
|---|---|---|---|
| 4,276,885 A | 7/1981 | Tickner et al. | |
| 4,544,545 A | 10/1985 | Ryan et al. | |
| 4,684,479 A | 8/1987 | D'Arrigo | |
| 4,900,540 A | 2/1990 | Ryan et al. | |
| 5,215,680 A | 6/1993 | D'Arrigo | |
| 5,228,446 A | 7/1993 | Unger | |
| 5,352,435 A | 10/1994 | Unger | |
| 5,487,390 A | 1/1996 | Cohen et al. | |
| 6,110,444 A | 8/2000 | Klaveness et al. | |
| 6,139,819 A | 10/2000 | Unger et al. | |
| 7,897,141 B2 | 3/2011 | Wheatley et al. | |
| 8,715,622 B2 | 5/2014 | Wheatley et al. | |
| 9,220,709 B2 | 12/2015 | Wheatley et al. | |
| 2004/0146516 A1 | 7/2004 | Roben et al. | |
| 2005/0084538 A1 | 4/2005 | Dayton et al. | |
| 2007/0110674 A1 | 5/2007 | Xu et al. | |
| 2008/0089848 A1 | 4/2008 | DiMauro | |
| 2008/0175893 A1 | 7/2008 | Huang et al. | |
| 2008/0247957 A1 | 10/2008 | Wheatley | |
| 2008/0279783 A1 | 11/2008 | Wheatley et al. | |
| 2009/0028797 A1 | 1/2009 | Wheatley et al. | |
| 2009/0196827 A1 | 8/2009 | Wheatley et al. | |
| 2011/0125079 A1 | 5/2011 | Wheatley et al. | |
| 2014/0213702 A1 | 7/2014 | Wheatley et al. | |

FOREIGN PATENT DOCUMENTS

| | | | |
|---|---|---|---|
| EP | 0554213 A1 | 8/1993 | |
| WO | 9115244 A2 | 10/1991 | |
| WO | 9313809 A1 | 7/1993 | |
| WO | 9320802 A1 | 10/1993 | |

OTHER PUBLICATIONS

Freytag, T. et al., Improvement of the encapsulation efficiency of oligonucleotide-containing biodegradable microspheres, Journal of Controlled Release 69, Oct. 2000, 197-207.
Huang, S. et al., A method to co-encapsulate gas and drugs in liposomes for ultrasound-controlled drug delivery, Ultrasound in Med. & Biol. 34:8, Aug. 2008, 1272-1280.
Huang, et al., Liposomes in ultrasonic drug and gene delivery, Advanced Drug Delivery Reviews, 60(10), Jun. 2008, 1167-1176.
Kodoma, et al., Morphological study of acoustic liposomes using transmission electron microscopy, J. Electron Microscopy 59(3), 2010, 187-196.
Krasovitski, B. et al., Intramembrane cavitation as a unifying mechanism for ultrasound-induced bioeffects, Proc Nat'l Acad Sci USA 108:8, Feb. 2011, 3258-3263.
Leong-Poi, H. et al., Noninvasive assessment of angiogenesis by ultrasound and microbubbles targeted to alpha(v)-integrins, Circulation 107(3), Jan. 2003, 455-460.
Pitt, et al., On Bubbles and Liposomes, J. Controlled Release, 125(2), Jan. 2008, 174-177.
Schroeder, A. et al., Ultrasound, liposomes, and drug delivery: principles for using ultrasound to control the release of drugs from liposomes, Chemistry and Physics of Lipids 162, Nov. 2009, 1-16.
Suzuki, et al., Effective gene delivery with novel liposomal bubbles and ultrasonic destruction technology, International Journal of Pharmaceutics, 354(1-2), Apr. 2008, 49-55.
Takahashi, M. et al., Spinal gene transfer using ultrasound and microbubbles, Journal of Controlled Release 117, Feb. 2007, 267-272.
Wrenn, S.P. et al., Bubble nucleation in lipid bilayers: a mechanism for low frequency ultrasound disruption, Biochimica et Biophysica Acta 1828, Apr. 2013, 1192-1197.

*Primary Examiner* — Michael G. Hartley
*Assistant Examiner* — Leah H Schlientz
(74) *Attorney, Agent, or Firm* — Saul Ewing Arnstein & Lehr LLP; Kathryn Doyle; Domingos J. Silva

(57) ABSTRACT

The present invention includes a construct that comprises at least one microbubble encapsulated within the aqueous core of a microcapsule. The present invention also includes a pharmaceutical composition comprising a construct comprising at least one microbubble encapsulated within the aqueous core of a microcapsule. The present invention further includes a method of imaging a tissue or organ in a subject, a method of delivering a therapeutic cargo to a tissue or organ in a subject, and a method of treating a disease or disorder in a subject.

37 Claims, 17 Drawing Sheets

Schematic Representation

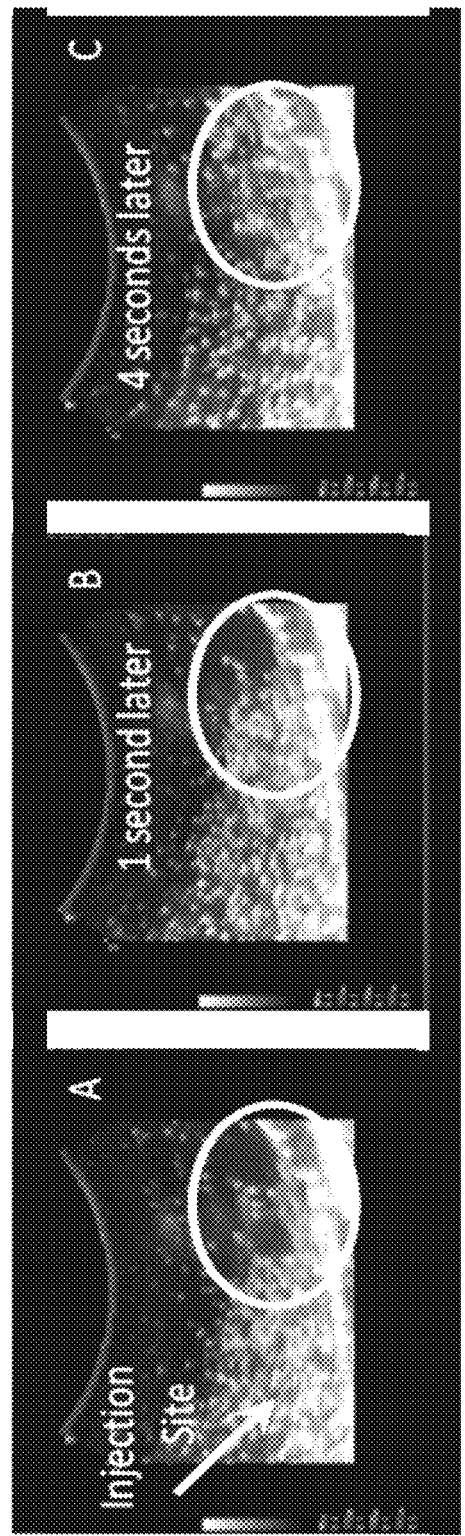

Figure 6A  Figure 6B
BEFORE ULTRASOUND | AFTER ULTRASOUND
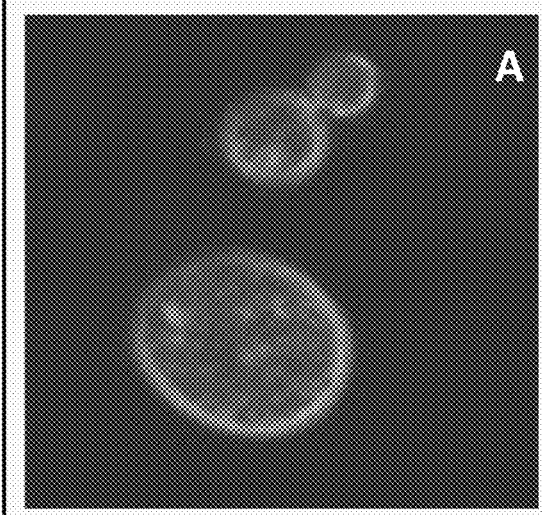
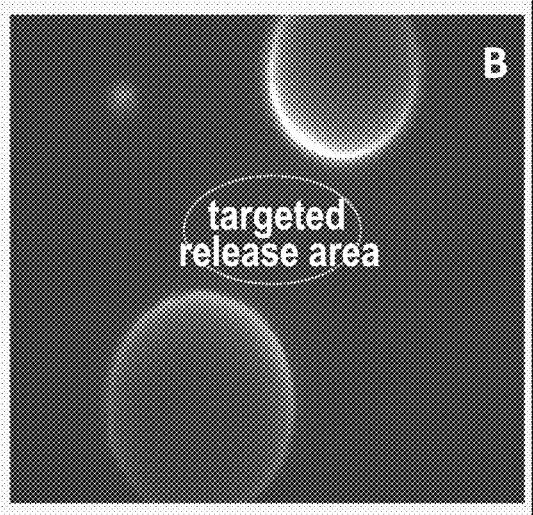
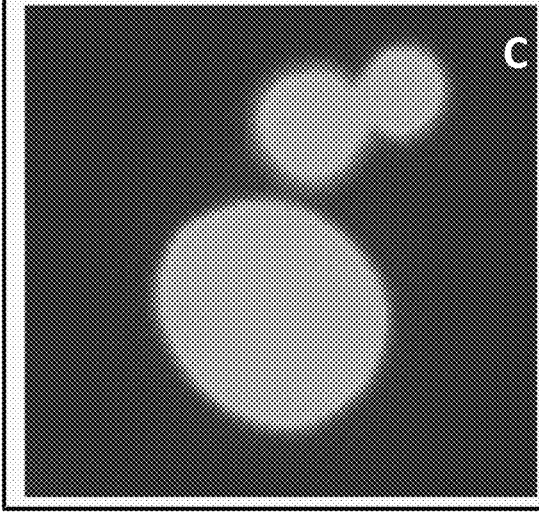
VISIBLE LIGHT
FLUORESCENCE
targeted release area
target is hit with dye!
Figure 6C  Figure 6D

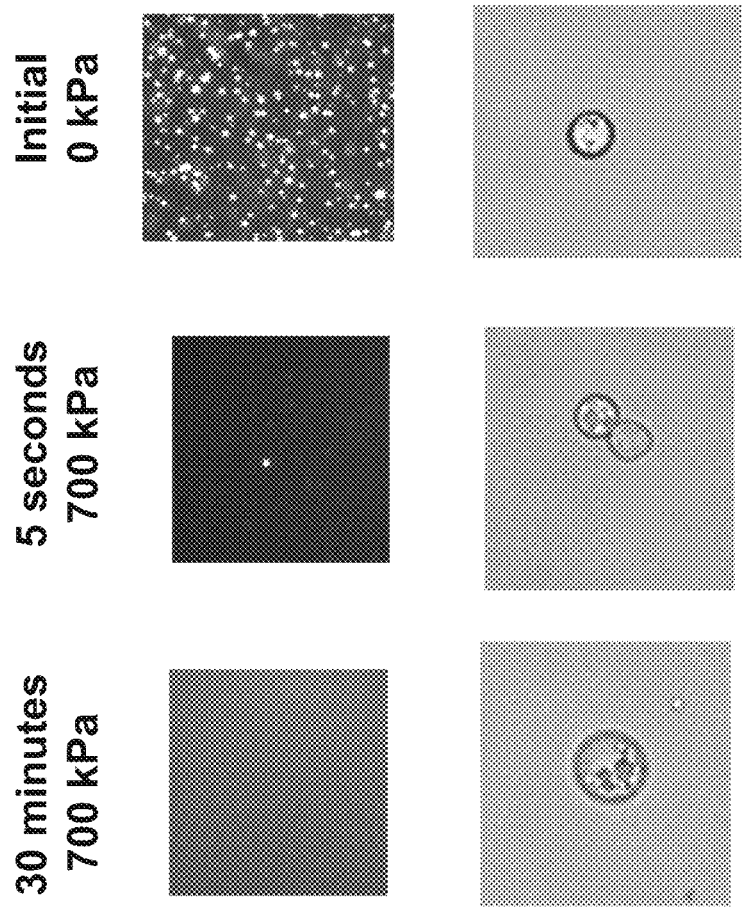

ENCAPSULATION OF MICROBUBBLES WITHIN THE AQUEOUS CORE OF MICROCAPSULES

CROSS-REFERENCE TO RELATED APPLICATIONS

The present application is a continuation of, and claims priority to, U.S. patent application Ser. No. 13/264,335, filed Jan. 12, 2012, now U.S. Pat. No. 10,258,563, which is a 35 U.S.C. § 371 national phase application from, and claiming priority to, International Application No. PCT/US2010/031772, filed Apr. 20, 2010, and published under PCT Article 21(2) in English, which claims priority under 35 U.S.C. § 119(e) to U.S. Provisional Application No. 61/170,830, filed Apr. 20, 2009, which applications are incorporated herein by reference herein in their entireties.

STATEMENT REGARDING FEDERALLY SPONSORED RESEARCH OR DEVELOPMENT

This invention was made with government support under Grant No. CBET-0346638, awarded by the National Science Foundation. The government therefore has certain rights in this invention.

BACKGROUND OF THE INVENTION

Ultrasound contrast agents used for enhancement of ultrasonic images have gone through several generations of development (Postema et al., 2006, Expert. Rev. MoJ. Diag. 6:493-501). The common feature is a gas core plus a stabilizing shell. First-generation agents comprised air plus a shell of albumin, lipid, or acrylate. Second-generation agents improved upon the first-generation by employing gases other than air, typically fluorinated compounds (octafluoropropane, perfluorobutane, or sulfur hexafluoride). Owing to lower solubility in water and slower diffusivity of these gases relative to air, microbubbles produced from these gases were more long-lived than their first-generation counterparts. Third-generation agents built upon the second-generation agents by incorporating into the stabilizing shell a species that conveys added stability (e.g., charged surfactants or PEGylated lipids to prevent microbubble coalescence) or targets a specific receptor within tissue (via receptor ligands, analogous to avidin-biotin binding). More recent research activity has involved design of microbubbles along similar lines but for the purpose of targeted or controlled drug delivery, rather than for imaging (Lum et al., 2006, J. Control Release 111:128-134; Klibanov et al., 1994, Adv. Drug Deliv. Rev. 37:139-157; Kheirolomoom et al., 2007, J. Control Release 118:275-284; Unger et al., 2002, Eur. J. Radiol. 42:160-168).

There is a long felt need in the art for novel compositions with unique properties that may act as both superior ultrasound contrast agents and targeted drug delivery vehicles. The present invention fulfills this need.

SUMMARY OF THE INVENTION

The invention includes a construct comprising at least one microbubble encapsulated within an aqueous core of an echo genie micro capsule. The shell of the microcapsule becomes permeable when irradiated with an ultrasound intensity that is equal to or higher than the leakage threshold intensity of the microcapsule.

In one embodiment, the shell of the microcapsule comprises self-assembling molecules. In another embodiment, the shell comprises phospholipids. In yet another embodiment, the shell comprises a giant unilamellar vesicle (GUY). In yet another embodiment, the shell comprises a polymer. In yet another embodiment, the shell of the microcapsule further comprises from about 0.001% to about 10% of an oil. In yet another embodiment, the oil is olive oil. In yet another embodiment, the aqueous core comprises a therapeutic agent.

In one embodiment, the at least one microbubble is free-floating in the aqueous core. In another embodiment, the at least one microbubble is tethered to the inner face of the microcapsule. In yet another embodiment, the microbubble comprises a shell. In yet another embodiment, the shell of the microbubble comprises a saturated phospholipid. In yet another embodiment, the shell of the microbubble comprises between about 0.001% and about 10% of a PEGylated lipid. In yet another embodiment, the microbubble comprises a gas. In yet another embodiment, the gas comprises a chemical selected from the group consisting of air, octafluoropropane, perfluorobutane and sulfur hexafluoride.

The invention also includes a pharmaceutical composition comprising a construct comprising at least one microbubble encapsulated within an aqueous core of an echogenic microcapsule. The shell of the microcapsule becomes permeable when irradiated with an ultrasound intensity that is equal to or higher than the leakage threshold intensity of the microcapsule.

In one embodiment, the shell of the microcapsule comprises self-assembling molecules. In another embodiment, the shell comprises phospholipids. In yet another embodiment, the shell comprises a giant unilamellar vesicle (GUY). In yet another embodiment, the shell comprises a polymer. In yet another embodiment, the shell of the microcapsule further comprises from about 0.001% to about 10% of an oil. In yet another embodiment, the oil is olive oil. In yet another embodiment, the aqueous core comprises a therapeutic agent.

In one embodiment, the at least one microbubble is free-floating in the aqueous core. In another embodiment, the at least one microbubble is tethered to the inner face of the microcapsule. In yet another embodiment, the microbubble comprises a shell. In yet another embodiment, the shell of the microbubble comprises a saturated phospholipid. In yet another embodiment, the shell of the microbubble comprises between about 0.001% and about 10% of a PEGylated lipid. In yet another embodiment, the microbubble comprises a gas. In yet another embodiment, the gas comprises a chemical selected from the group consisting of air, octafluoropropane, perfluorobutane and sulfur hexafluoride.

The invention further includes a method of imaging a tissue or an organ in a subject. The method comprises the step of administering to the subject a pharmaceutical composition comprising a construct comprising at least one microbubble encapsulated within an aqueous core of an echogenic microcapsule. The location of the construct within the subject is then monitored by ultrasound techniques using a first ultrasound intensity, wherein the first ultrasound intensity is lower than the leakage threshold intensity of the microcapsule.

In one embodiment, the shell of the microcapsule comprises self-assembling molecules. In another embodiment, the shell comprises phospholipids. In yet another embodiment, the shell comprises a giant unilamellar vesicle (GUV).

In yet another embodiment, the shell comprises a polymer. In yet another embodiment, the shell of the microcapsule further comprises from about 0.001% to about 10% of an oil. In yet another embodiment, the oil is olive oil. In yet another embodiment, the aqueous core comprises a therapeutic agent.

In one embodiment, the at least one microbubble is free-floating in the aqueous core. In another embodiment, the at least one microbubble is tethered to the inner face of the microcapsule. In yet another embodiment, the microbubble comprises a shell. In yet another embodiment, the shell of the microbubble comprises a saturated phospholipid. In yet another embodiment, the shell of the microbubble comprises between about 0.001% and about 10% of a PEGylated lipid. In yet another embodiment, the microbubble comprises a gas. In yet another embodiment, the gas comprises a chemical selected from the group consisting of air, octafluoropropane, perfluorobutane and sulfur hexafluoride.

The invention also includes a method of delivering a therapeutic cargo to a tissue or organ in a subject. The method comprises the steps of administering to the subject a pharmaceutical composition comprising a construct comprising at least one microbubble encapsulated within an aqueous core of an echogenic microcapsule. The location of the construct within the subject is then monitored by ultrasound techniques using a first ultrasound intensity, wherein the first ultrasound intensity is lower than the leakage threshold intensity of the microcapsule. The presence of presence of the construct in the vicinity of the organ or tissue is then detected based on ultrasound monitoring. The cargo is then released from the construct by applying a second ultrasound intensity to the construct, wherein the second ultrasound intensity is equal to or higher than the leakage threshold of the microcapsule, and equal to or lower than the maximum ultrasound intensity that can be safely applied to the tissue or organ.

In one embodiment, the shell of the microcapsule comprises self-assembling molecules. In another embodiment, the shell comprises phospholipids. In yet another embodiment, the shell comprises a giant unilamellar vesicle (GUV). In yet another embodiment, the shell comprises a polymer. In yet another embodiment, the shell of the microcapsule further comprises from about 0.001% to about 10% of an oil. In yet another embodiment, the oil is olive oil. In yet another embodiment, the aqueous core comprises a therapeutic agent.

In one embodiment, the at least one microbubble is free-floating in the aqueous core. In another embodiment, the at least one microbubble is tethered to the inner face of the microcapsule. In yet another embodiment, the microbubble comprises a shell. In yet another embodiment, the shell of the microbubble comprises a saturated phospholipid. In yet another embodiment, the shell of the microbubble comprises between about 0.001% and about 10% of a PEGylated lipid. In yet another embodiment, the microbubble comprises a gas. In yet another embodiment, the gas comprises a chemical selected from the group consisting of air, octafluoropropane, perfluorobutane and sulfur hexafluoride.

The invention further includes a method of treating a disease or disorder in a subject in need thereof. The method comprises the step of administering to the subject an effective amount of a pharmaceutical composition comprising a construct comprising at least one microbubble encapsulated within an aqueous core of an echogenic microcapsule. The location of the construct within the subject is then monitored by ultrasound methods using a first ultrasound intensity, wherein the first ultrasound intensity is lower than the leakage threshold intensity of the microcapsule. The presence of the construct in the vicinity of an organ or tissue that is associated with the disease or disorder is then detected based on ultrasound monitoring. The cargo is then released from the construct by applying a second ultrasound intensity to the construct, wherein the second ultrasound intensity is equal to or higher than the leakage threshold of the microcapsule, and equal to or lower than the maximum ultrasound intensity that can be safely applied to the tissue or organ.

In one embodiment, the shell of the microcapsule comprises self-assembling molecules. In another embodiment, the shell comprises phospholipids. In yet another embodiment, the shell comprises a giant unilamellar vesicle (GUV). In yet another embodiment, the shell comprises a polymer. In yet another embodiment, the shell of the microcapsule further comprises from about 0.001% to about 10% of an oil. In yet another embodiment, the oil is olive oil. In yet another embodiment, the aqueous core comprises a therapeutic agent.

In one embodiment, the at least one microbubble is free-floating in the aqueous core. In another embodiment, the at least one microbubble is tethered to the inner face of the microcapsule. In yet another embodiment, the microbubble comprises a shell. In yet another embodiment, the shell of the microbubble comprises a saturated phospholipid. In yet another embodiment, the shell of the microbubble comprises between about 0.001% and about 10% of a PEGylated lipid. In yet another embodiment, the microbubble comprises a gas. In yet another embodiment, the gas comprises a chemical selected from the group consisting of air, octafluoropropane, perfluorobutane and sulfur hexafluoride.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1A is a schematic representation of a construct of the invention.

Symbols: (1) microcapsule aqueous core; (2) microcapsule shell; (3) microbubble shell; (4) microbubble gas core; (5a) hydrophilic or hydrophobic therapeutic agent; (5b) hydrophobic therapeutic agent. FIG. 1B is a photomicrograph of a construct of the invention, wherein the microbubbles appear as white dots.

FIG. 2C illustrates a pulse train that may be used to excite microbubble samples.

FIG. 3A illustrates an acoustic spectrogram obtained at ~50 kPa of transmitting transducer. The primary transducer frequency was observed as a bright, horizontal white line at 1.8 MHz. Also evident were harmonics (faint, horizontal white stripes) at multiples of the primary frequency; these were indicative of non-linear processes, including non-linear wave propagation in water and non-linear microbubble oscillations (i.e., stable cavitation). FIG. 3B illustrates an acoustic spectrogram obtained at a power of ~1 MPa of transmitting transducer. The phenomenon observed in FIG. 3A was also observed here. However, a sub harmonic (horizontal white stripe) at one half the primary frequency was also observed. This is an indication, but not proof, of inertial cavitation. Vertical white stripes, which constitute broadband noise, were observed, and were evidence of inertial cavitation.

FIGS. 5A-5C illustrate brightness (B-Mode) images of poly(lactic acid) microcapsules with encapsulated microbubbles in 0.9% saline solution. Images were taken immediately (FIG. 5A), 1 second (FIG. 5B), and 4 seconds (FIG. 5C) after injection of microcapsules. Figure 5A illustrates the injection site. Flow direction was from left to right. Transducer imaging frequency was 5 MHz. Scattering from microcapsules was evident versus saline as a background. The acoustic activities of this Figure suggest that the brightness observed here stems—at least in part—from microbubble oscillations.

FIGS. 6A-6D illustrate controlled drug delivery using ultrasound activation of a construct of the invention. In FIG. 6A, under visible light microscopy, microbubbles may be observed within the microcapsules. In FIG. 6C, under fluorescent conditions, a fluorescent dye within the same microcapsules may be observed. For comparative purposes, FIG. 6B illustrates microcapsules (without microbubbles) originally containing a fluorescent dye under visible light microscopy after 1 minute of ultrasound exposure (20 KHz); in FIG. 6D, the same microcapsules are shown under fluorescent conditions—the microcapsules no longer contain the fluorescent dye, which has leaked into the surrounding aqueous medium due to application of ultrasound.

FIG. 13 is a set of micrographs relating to freely flowing microbubbles (left column) and constructs of the invention (right column). Upon application of a pressure of 412 kPa, micrographs were registered at the initial time (top row), after 5 seconds (middle row) and after 30 minutes (bottom row). The unencapsulated microbubbles disappeared within seconds of constant pressure, but encapsulated microbubbles of the invention persisted for over 30 minutes.

DETAILED DESCRIPTION OF THE INVENTION

Figure 1A:
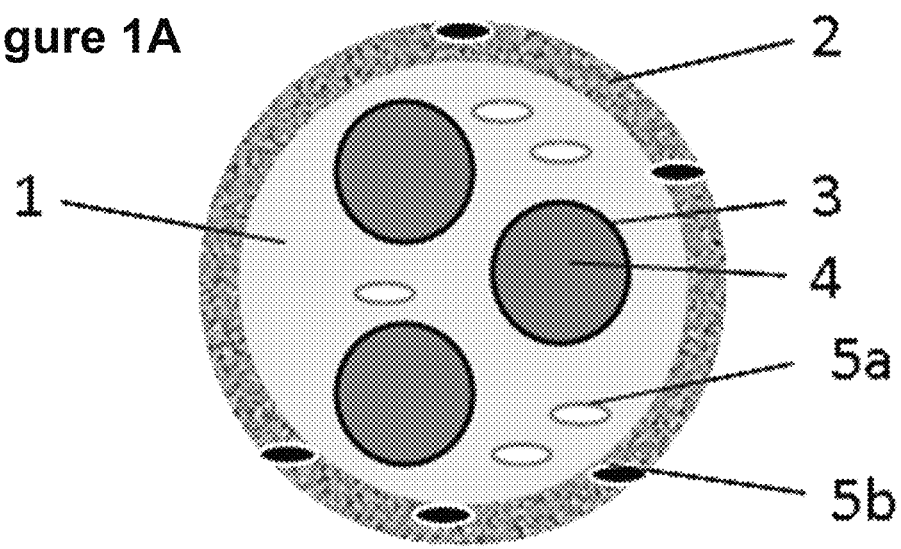
FIGS. 1A-1B illustrate a construct of the invention.

The present invention is based on the discovery of a novel construct that interacts with ultrasound in two distinct ways. In one embodiment, the present invention provides a construct that may be used as a long-lasting ultrasound contrast agent. In another embodiment, the present invention provides a construct that may be used in controlled drug delivery using ultrasound as a remote trigger.

In one embodiment, the present invention provides a method of performing a long-lasting ultrasound diagnostic test in a subject using a construct of the invention. In another embodiment, the present invention provides a method of delivering a therapeutic cargo to a tissue or organ in a subject using a construct of the invention. In yet another embodiment, the invention provides a method of treating a disease or disorder in a subject, wherein a construct of the invention is used to achieve controlled delivery of a therapeutic cargo. In yet another embodiment, the subject is a mammal, preferably a human.

Definitions

The definitions used in this application are for illustrative purposes and do not limit the scope used in the practice of the invention.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art.

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein, "about" when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein with respect to the construct of the invention, the term "echogenic" indicates that the construct is capable of producing a detectable echo when insonated with ultrasonic waves due to an acoustic impedance mismatch between the physiological environment and the microcapsule and/or construct.

As used herein, a "disease" is a state of health of subject wherein the subject cannot maintain homeostasis, and wherein if the disease is not ameliorated then the subject's health continues to deteriorate.

As used herein, a "disorder" is a state of health in which the subject is able to maintain homeostasis, but in which the subject's state of health is less favorable than it would be in the absence of the disorder. Left untreated, a disorder does not necessarily cause a further decrease in the subject's state of health.

As used herein, the term "treating" or "alleviating" means ameliorating the effects of, or delaying, halting or reversing the progress of a disease or disorder. The word encompasses reducing the severity of a symptom of a disease or disorder and/or the frequency of a symptom of a disease or disorder. In some embodiments, treatment may be applied after one or more symptoms have developed. In other embodiments, treatment may be administered in the absence of symptoms. For example, treatment may be administered prior to symptoms (e.g., in light of a history of symptoms and/or one or more other susceptibility factors), or after symptoms have resolved, for example to prevent or delay their reoccurrence.

As used herein, a "therapeutic agent" or "therapeutic drug" of the present invention is any agent, compound, or molecule useful in treating a disease or disorder.

As used herein, the term "medical intervention" means a set of one or more medical procedures or treatments that are required for ameliorating the effects of, delaying, halting or reversing a disease or disorder of a subject. A medical intervention may involve surgical procedures or not, depending on the disease or disorder in question. A medical intervention may be wholly or partially performed by a medical specialist, or may be wholly or partially performed by the subject himself or herself, if capable, under the supervision of a medical specialist or according to literature or protocols provided by the medical specialist.

As used herein, the term "subject" or "patient" or "individual" refers to a human or a non-human mammal. Non-human mammals include, for example, livestock and pets, such as ovine, bovine, porcine, canine, feline and murine mammals. In one embodiment, the subject is canine, feline or human. In another embodiment, the subject is human.

As used herein, the term "effective amount" or "therapeutically effective amount" refers to a non-toxic but sufficient amount of the composition used in the practice of the invention that is effective to, in non-limiting examples, provide imaging contrast to a subject or treat a disorder or disease in a subject. The desired treatment may be diagnostic, prophylactic and/or therapeutic. That result may be imaging of an organ or tissue in the subject; or reduction and/or alleviation of the signs, symptoms, or causes of a disease or disorder, or any other desired alteration of a biological system. An appropriate therapeutic amount in any individual case may be determined by one of ordinary skill in the art using routine experimentation.

As used herein as applied to a given molecule, the term "specifically binds" refers to the recognition and binding of the given molecule to another molecule or feature, wherein the given molecule does not substantially recognize or bind other molecules or features in a sample.

As used herein, the phrase "inhibit" means to reduce a molecule, a reaction, an interaction, a gene, an mRNA, and/or a protein's expression, stability, function or activity by a measurable amount or to prevent this phenomenon entirely. Inhibitors are compounds that, for example, bind to, partially or totally block stimulation, decrease, prevent, delay activation, inactivate, desensitize, or down-regulate a protein, a gene, and an mRNA stability, expression, function and activity, e.g., antagonists.

As used herein, a "therapeutic cargo" refers to a therapeutic agent or therapeutic drug that is associated with the construct of the invention and may be released at a desired location at a desired time by irradiation of the construct with ultrasound. The therapeutic cargo may be dissolved with the aqueous core, or otherwise attached to, the drug delivery construct. The construct of the instant invention is echogenic and therefore may also act as a contrast agent. The therapeutic cargo is specifically released upon the application of ultrasound of appropriate frequency, intensity and focusing to the construct of the invention comprising the cargo.

The term "phospholipids" refers to any member of a large class of fatlike organic compounds that in their molecular structure resemble the triglycerides, except for the replacement of a fatty acid with a phosphate-containing polar group. One end of the molecule is soluble in water (hydrophilic) and water solutions. The other, fatty acid, end is soluble in fats (hydrophobic).

As used herein, the term "polypeptide" refers to a polymer composed of amino acid residues, related naturally occurring structural variants, and synthetic non-naturally occurring analogs thereof linked via peptide bonds. Synthetic polypeptides may be synthesized, for example, using an automated polypeptide synthesizer. The terms "protein" and "peptide" refer interchangeably to polypeptides.

As used herein, the term "pharmaceutically acceptable" refers to a material, such as a carrier or diluent, which does not abrogate the biological activity or properties of the construct, and is relatively non-toxic, i.e., the material may be administered to an individual without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids and bases, including inorganic acids, inorganic bases, organic acids, inorganic bases, solvates, hydrates, and clathrates thereof.

As used herein, the term "composition" or "pharmaceutical composition" refers to a mixture of at least one construct of the invention with a pharmaceutically acceptable carrier. The pharmaceutical composition facilitates administration of the construct to a subject. Multiple techniques of administering a construct exist in the art including, but not limited to, intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a construct of the present invention within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the construct of the invention, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations, "Pharmaceutically acceptable carrier" also includes any and all coatings, antibacterial and antifungal agents, and absorption delaying agents, and the like that are compatible with the activity of the construct, and are physiologically acceptable to the subject. Supplementary active compounds may also be incorporated into the compositions. The "pharmaceutically acceptable carrier" may further includes a pharmaceutically acceptable salt of any component of the construct, such as the therapeutic drug. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the construct's ability to perform its intended function, e.g., treating, ameliorating, or preventing a disease or disorder in a subject.

As used herein, the term "applicator" is used to identify any device including, but not limited to, a hypodermic syringe, a pipette, and the like, for administering the constructs and compositions used in the practice of the invention.

Construct of the Invention

The present invention encompasses a novel construct that may be used as a superior, long-lasting ultrasound contrast agent as well as delivery agent of a therapeutic cargo to a desired location under controllable release conditions.

The construct may be used as a long-lasting ultrasound contrast agent. The present invention also provides a construct that may be used as a drug delivery agent. In an aspect, the construct of the invention is cleared by the body at a lower rate than the corresponding unencapsulated microbubble. In another aspect, the microbubble within the construct of the invention does not dissolve in the body fluids due to its encapsulation within the microcapsule. In a non-limiting example, the construct of the invention is illustrated in FIG. 1.

The construct of the invention comprises at least one microbubble encapsulated within the aqueous core of a microcapsule. The shell of the microcapsule, which may contain a small amount of oil, is designed to be impervious to the gas contained within the microbubbles and a drug, at low ultrasound intensities (imaging mode) but not at high ultrasound intensities (drug delivery mode).

Because the phospholipid-coated microbubbles are encapsulated within an aqueous compartment that is itself surrounded by an impervious microcapsule shell, the microbubbles do not dissolve (as they otherwise would if not encapsulated) when ultrasound (a pressure wave) is applied. For example, at an external pressure that causes unencapsulated phospholipid-coated microbubbles to dissolve within a few seconds, the constructs of the invention persist for at least 30 minutes (FIG. 13); that translates to at least a 600-fold increase in microbubble longevity using the construct disclosed herein.

Figure 8:
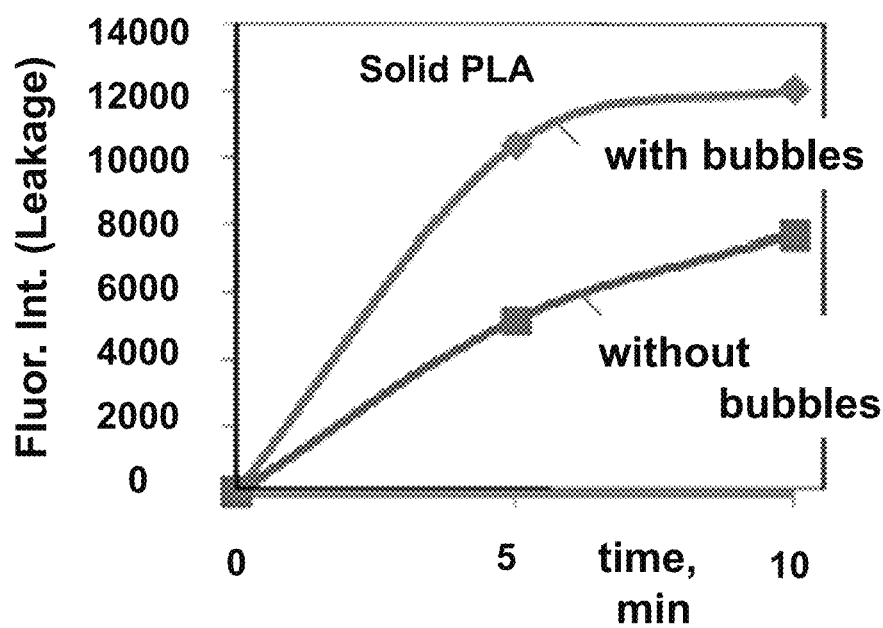
FIG. 8 illustrates ultrasound-induced leakage profiles from poly(lactic acid) microcapsules. Given the large diameter of these particles (5-50 microns), direct interaction with the ultrasound field may cause leakage in the absence of externally added microbubbles. Nevertheless, the presence of encapsulated microbubbles doubles the extent of leakage. Error bars from experimental data are omitted for clarity. All % s are mole % s.
Figure 15:
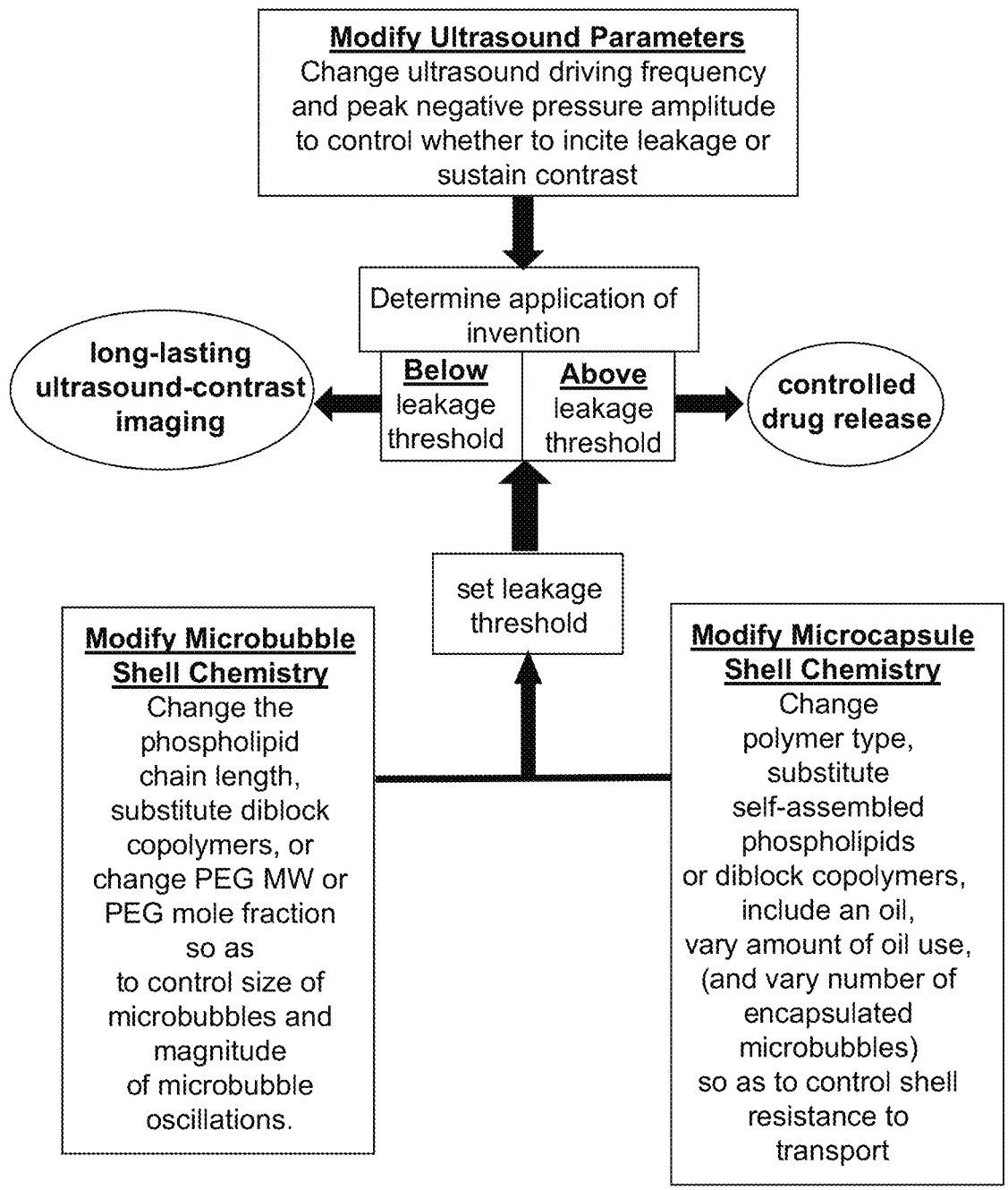
FIG. 15 is a schematic diagram illustrating experimental steps that may be taken to prepare a construct with a particular leakage threshold in response to ultrasound, as a means of preparing a long-lasting ultrasound-contrast imaging agent or effecting drug release.

At ultrasound intensities used for drug delivery (those intensities above the "leakage threshold" of the construct), the shell of the microcapsule shell is no longer impervious, i.e., becomes permeable. Application of ultrasound above the leakage threshold induces transport of the drug across the microcapsule shell, thereby facilitating drug release from the microcapsule into the bulk phase (which may be the bloodstream of a subject). The leakage threshold is a characteristic property of the construct of the invention and may be manipulated by changing parameters such as, but not limited to, the nature of the microcapsule shell (which may comprise self-assembling molecules, such as polymers or phospholipids), the presence of oil in the microcapsule shell, the number of microbubbles encapsulated with the microcapsule, the nature of the material used in the assembly of the microbubble shell, the length of the phospholipid chain in the microbubble shell, the PEG molecular weight or PEG mole fraction used in the microbubble shell (FIG. 15). Variations in these parameters, as well as other parameters that affect microcapsule or microbubble structure as described within the present disclosure or known to those skilled in the art, allows one skilled in the art to vary the leakage threshold for a given construct. The leakage threshold for a given construct may be determined by a method such as that described in FIG. 8. In one embodiment, the leakage threshold is selected as the acoustic pressure that over the period of 30 minutes affords between about 5% and about 10% of the maximum release of drug possible. In another embodiment, the leakage threshold is selected as the acoustic pressure that over the period of 30 minutes affords between about 10% and about 20% of the maximum release of drug possible. In yet another embodiment, the leakage threshold is selected as the acoustic pressure that over the period of 30 minutes affords between about 20% and about 40% of the maximum release of drug possible. In yet another embodiment, the leakage threshold is selected as the acoustic pressure that over the period of 30 minutes affords between about 40% and about 60% of the maximum release of drug possible. In yet another embodiment, the leakage threshold is selected as the acoustic pressure that over the period of 30 minutes affords between about 60% and about 80% of the maximum release of drug possible. In yet another embodiment, the leakage threshold is selected as the acoustic pressure that over the period of 30 minutes affords between about 80% and about 1000% of the maximum release of drug possible.

In one embodiment, no release is observed in the absence of ultrasound, but application of ultrasound at frequency of 2.25 MHz and a peak negative pressure of nominally 0.5 MPa produces significant release within one minute. In an embodiment, the construct of the invention is used for controlled drug delivery at ultrasound frequencies ranging from about 1 to about 10 MHz. In another embodiment, the construct of the invention is used for controlled drug delivery at ultrasound frequencies ranging from about 1 to about 8 MHz. In yet another embodiment, the construct of the invention is used for controlled drug delivery at ultrasound frequencies ranging from about 1 to about 5 MHz. In yet another embodiment, the construct of the invention is used for controlled drug delivery at ultrasound frequencies ranging from about 2 to about 5 MHz.

The construct of the invention comprises a microcapsule. The outer physical limits of the microcapsule are defined by a shell, which separates the aqueous core of the microcapsule and the contents thereof from any surrounding fluid or tissue. In one embodiment, at least one microbubble is encapsulated within the aqueous core of the microcapsule. In one aspect, the shell of the microcapsule ensures long-lasting ultrasound contrast by preventing dissolution of the contents of the microbubble into the surrounding fluid. In another aspect, the shell of the microcapsule avoids undesirable contact of the contents of the microcapsule with fluid or tissue surrounding the microcapsule until high-intensity ultrasound is applied.

In one embodiment, the shell of the microcapsule comprises self-assemblying molecules. The self-assembling molecules useful within the invention comprise a di-block copolymer, phospholipid, liposome, unilamellar vesicle, giant unilamellar vesicle (GUV), or any other phospholipid microcapsule. In another embodiment, the shell of the microcapsule comprises a polymer shell. The polymer shell may comprise a biocompatible and biodegradable polymer, such as, but not limited to, polyhydroxy acid polymers (such as poly-lactic-co-glycolic acid and poly-L-lactic acid) and ethylcellulose.

The shell may further comprise an oil. The oil should be physiologically compatible and liquid at room temperature. In one embodiment, the shell further comprises from about 0.001% to about 10% of the oil. In another embodiment, the oil is olive oil, sunflower oil or sesame oil. In yet another embodiment, the oil is olive oil.

In one embodiment, the microbubble encapsulated within the aqueous core of the microcapsule is free floating. In another embodiment, the microbubble encapsulated within the aqueous core of the microcapsule is tethered to the inner wall of the microcapsule.

The outer physical limits of the microbubble are defined by a shell. In one embodiment, the shell of the microbubble comprises a saturated phospholipid. In another embodiment, the shell of the microbubble comprises between about 0.001% and about 10% of a PEGylated lipid. In one aspect, the shell of the microbubble slows gas diffusion in the absence of ultrasound. In another aspect, the shell of the microbubble avoids aggregation of multiple microbubbles within the aqueous core of microcapsules.

In one embodiment, the microbubble encapsulated within the aqueous core comprises a gas. The gas may be any gas that is biocompatible and enhances the echogenic property of the construct of the invention. Examples of gases useful in the practice of the invention include, but are not limited to, air, nitrogen gas, carbon dioxide and fluorinated compounds such as octafluoropropane, perfluorobutane, and sulfur hexafluoride.

In one embodiment, the microbubble may further comprise stabilizing agents in order to increase longevity of the microbubbles. Examples of stabilizing agents include, but are not limited to, charged surfactants, PEGylated phospholipids, DMPC (dimyristoylphosphatidylcholine), DSPC (distearoylphosphatidylcholine), and egg PC (egg phosphatidylcholine).

Microbubbles

Phospholipids may be used in the synthesis of the microbubble shell due to their inherent biocompatibility. Moreover, phospholipid vesicles serve as cell membrane mimics. In fact, cholesterol-rich domains, found in cell membranes and known as "lipid rafts," play a role in sonoporation. One particular aspect of microbubble synthesis relates to the "chain melting temperature" or "gel transition temperature" of a phospholipid (the temperature at which the phospholipid changes between a liquid and a gel phase). The gel transition temperature of a phospholipid depends on chain length (the number of methylene units) and chain unsaturation (the number of carbon-carbon double bonds) of the phospholipids. Synthesis of stable microbubbles requires that a phospholipid be in the gel phase. For example, DSPC exists as a gel phase at body temperature but becomes ineffective as a shell material at temperatures above 60° C. DMPC may also be used, if the temperature of application is below 25° C.

Table 1 lists three phospholipid species, along with their gel transition temperatures, and the results of experiments attempting to make stable microbubbles with these species at different temperatures. All microbubble formulations included 5 mol % PEG6000MS.

In all cases in which the processing temperature was below the gel transition temperature, irrespective of the phospholipid identity, microbubble synthesis was feasible. Conversely, microbubble synthesis at temperatures greater than the gel transition temperature was not feasible, regardless of which phospholipid was used.

TABLE 1

Influence of gel transition temperature on survival of microbubbles.

| Phospholipid species | Gel transition temperatures (° C.) | 7° C. | 37° C. | 60° C. |
| --- | --- | --- | --- | --- |
| Egg PC | −10 | No | No | No |
| DMPC | 23 | Yes | No | No |
| DSPC | 56 | Yes | Yes | No |

Use of a gel-phase lipid is required to prevent gas from escaping the microbubble. When microbubbles were made with phospholipids in a gel phase and then heated above the phospholipid chain melting temperature, they swelled significantly from an initial diameter of several microns to a final size that was hundreds of microns in diameter. Indeed, these microbubbles expanded so as to fill the capillary in which they were contained and therefore became nonspherical, taking on the geometry of the capillary itself. Microbubbles made from DMPC at 7° C. grew spontaneously upon heating to 37° C. Similar growth occurred for microbubbles made from egg PC at 7° C. No such growth was observed for DSPC, which remained in the gel phase at these temperatures. Such growth may have resulted from simple expansion of individual microbubbles or by inward diffusion of gas. However, growth did not appear to involve coalescence or fusion of multiple microbubbles.

In addition to phospholipid species, microbubble behavior and stability also appear to depend somewhat on processing conditions. Although difficult to quantify, higher sonication intensities during gas delivery appear to lead to higher microbubble yields and more stable (longer-lasting or more diffusion-resistant) microbubble populations. Other parameters may also be at play in this process. In a non-limiting aspect, this observation may be explained by tighter lipid chain packing resulting from higher peak pressures at higher sonication powers.

In one embodiment, the shell of the microbubbles incorporates PEGylated lipids. The gel-phase phospholipid may prevent excessive gas escape from a single microbubble, but "naked" DSPC microbubbles coalesce into clusters of microbubbles. An added shell component should preferably prevent excessive coalescence of multiple microbubbles. The coalescence may be avoided by including a PEGylated lipid, in which steric hindrance of polymer chains inhibits close approach of adjacent microbubbles. In a non-limiting embodiment, 5 mol % PEG6000MS is used. In a non-limiting example, a PEGylated phosphatidylcholine with a PEG molecular weight of 2000 was ineffective in forming stable microbubbles. Interestingly, PEG2000MS was able to afford stable microbubbles, although the PEG molecular weight did influence microbubble susceptibility to cavitation as compared with PEG6000MS. In another embodiment, microbubble coalescence may be avoided by inclusion of negatively charged phospholipids, whereby electrostatic forces cause microbubbles to repel upon close approach.

The microbubbles may contain a pharmacological agent or agent-carrying reservoir in the shell or more preferably in the central core. The cores of the microbubbles may contain a physiologically compatible gas such as air, carbon dioxide, nitrogen or a perfluorocarbon.

Therapeutic Agents

In one embodiment, the microcapsule of the invention comprises a therapeutic agent. The therapeutic agent may be a hydrophilic agent or a hydrophobic agent. A hydrophilic agent may be dissolved in molecular form within the aqueous core. A hydrophobic agent may be dispersed in the aqueous core in colloidal form (e.g., as surfactant-stabilized micelles), or may be dispersed in the microcapsule shell.

The types of agents to be released from the microbubble agent may be, for example, cardiovascular drugs (endocardium agents) with short circulatory half-lives that affect the cardiac tissues, vasculature and endothelium to protect and treat the heart from ischemic or reperfusion injury or coronary artery from restenosis (anti-restenosis agent). The agents may also be anti-cancer agents, such as antimetabolites (azathiopurine, mercaptopurine), doxorubicin, epirubicin, bleomycin, vinca alkaloids, taxanes, and topoisomerase inhibitors (camptothecins, irinotecan, topotecan, amsacrine, etoposide, teniposide), among others. Drugs that target platelets (anti-platelet agent) and white cells (anti-white cell agent), which may plug the microvasculature of the heart after a heart attack, may also be useful for local cardiac delivery. The construct of the invention may also be used to deliver compounds such as lutein, zeaxanthin and omega-3 fatty acids, useful in the treatment of macular degeneration. The construct of the invention may further be used to deliver compounds that are active at the systemic level (such as insulin) in a controllable and titratable dose.

Another type of drug useful for local delivery is a drug for which a local effect is required but where systemic effects of the drug would be detrimental. These are typically drugs with high toxicity, for example, locally administered potent vasodilators that would increase blood flow to hypoxic tissue but, if delivered systemically, would cause a dangerous drop in blood pressure. Suitable drugs include, but are not limited to: fibronolytic agents, such as tissue plasminogen activator, streptokinase, urokinase, and their derivatives; vasodilators such as verapamil; multifunctional agents, such as adenosine, adenosine agonists, adenosine monophosphate, adenosine diphosphate, adenosine triphosphate, and their derivatives; white cell or platelet acting agents, such as GPIIb/IIIa antagonists; energy conserving agents, such as calcium channel blockers, magnesium and beta blockers; endothelium acting agents, such as nitric oxide, nitric oxide donors, nitrates, and their derivatives; free-radical scavenging agents; agents that affect ventricular remodeling, such as ACE inhibitors and angiogenic agents; and agents that limit restenosis of coronary arteries after balloon angioplasty or stenting.

In addition to therapeutic agents delivered locally to the heart, the use of vasodilators in a construct of the invention may enhance diagnostics. Vasodilators are used in cardiology to assess the coronary blood flow reserve by comparing blood flow in the heart with and without the maximal vasodilation by the pharmacological agent. Coronary blood flow reserve correlates well with subject prognosis since the reserve capacity enables the myocardium to remain viable during a heart attack. Adenosine and other vasodilators are used during interventional cardiology and nuclear imaging to determine coronary reserve. A microbubble agent that contains a vasodilator may be useful in echocardiography to examine the myocardium under normal conditions, and then upon release of the vasodilator by the ultrasound beam conditions to stimulate local vasodilation. The coronary blood flow reserve may be estimated non-invasively using ultrasound imaging by the extent of hyperemia of the myocardium, Doppler regional flow, or by other well known methods of characterizing the ultrasound imaging data.

Methods of the Invention

The invention includes a method of imaging a tissue or an organ in a subject. The method comprises the following steps. A pharmaceutical composition comprising a construct comprising at least one microbubble encapsulated within an aqueous core of an echogenic microcapsule is administered to the subject. The location of the construct within the subject is then monitored by ultrasound techniques using a first ultrasound intensity. The first ultrasound intensity is lower than the leakage threshold intensity of the at least one microcapsule.

The invention also includes a method of delivering a therapeutic cargo to a tissue or organ in a subject. The method comprises the following steps. A pharmaceutical composition comprising a construct comprising at least one microbubble encapsulated within an aqueous core of an echogenic microcapsule is administered to the subject. The location of the construct within the subject is then monitored by ultrasound techniques using a first ultrasound intensity.

The first ultrasound intensity is lower than the leakage threshold intensity of the at least one microcapsule. The presence of the construct in the vicinity of the organ or tissue is then detected based on ultrasound monitoring. The cargo is then released from the construct by applying a second ultrasound intensity to the construct. The second ultrasound intensity is: equal to or higher than the leakage threshold of the microcapsule, and equal to or lower than the maximum ultrasound intensity that can be safely applied to the tissue or organ.

The invention further includes a method of treating a disease or disorder in a subject in need thereof. The method comprises the following steps. An effective amount of a pharmaceutical composition comprising a construct comprising at least one microbubble encapsulated within an aqueous core of an echogenic microcapsule is administered to the subject. The location of the construct within the subject is then monitored by ultrasound methods using a first ultrasound intensity. The first ultrasound intensity is lower than the leakage threshold intensity of the microcapsule. The presence of the construct in the vicinity of an organ or tissue that is associated with the disease or disorder is then detected based on ultrasound monitoring. The cargo is then released from the construct by applying a second ultrasound intensity to the construct. The second ultrasound intensity is: equal to or higher than the leakage threshold of the microcapsule, and equal to or lower than the maximum ultrasound intensity that can be safely applied to the tissue or organ.

In one embodiment, the microcapsule comprises a shell comprising self-assembling molecules. In another embodiment, the shell of the microcapsule comprises phospholipids. In yet another embodiment, the shell of the microcapsule comprises a giant unilamellar vesicle (GUV). In yet another embodiment, the shell of the microcapsule comprises a polymer. In yet another embodiment, the shell of the microcapsule further comprises from about 0.001 to about 10% of an oil. In yet another embodiment, the oil is olive oil. In yet another embodiment, the aqueous core comprises a therapeutic agent. In yet another embodiment, the at least one microbubble is free-floating in the aqueous core. In yet another embodiment, the at least one microbubble is tethered to the inner face of the microcapsule. In yet another embodiment, the microbubble comprises a shell. In yet another embodiment, the shell of the microbubble comprises a saturated phospholipid. In yet another embodiment, the shell of the microbubble comprises between about 0.001% and about 10% of a PEGylated lipid. In yet another embodiment, the microbubble comprises a gas. In yet another embodiment, the gas comprises a chemical selected from the group consisting of air, octafluoropropane, perfluorobutane and sulfur hexafluoride.

In one embodiment, the maximum ultrasound intensity that can be safely applied to the tissue or organ is about 20,000 watts/m$^2$. In another embodiment, the maximum ultrasound intensity that can be safely applied to the tissue or organ is about 15,000 watts/m$^2$. In yet another embodiment, the maximum ultrasound intensity that can be safely applied to the tissue or organ is about 10,000 watts/m$^2$. In yet another embodiment, the maximum ultrasound intensity that can be safely applied to the tissue or organ is about 7,500 watts/m$^2$. In yet another embodiment, the maximum ultrasound intensity that can be safely applied to the tissue or organ is about 5,000 watts/m$^2$. In yet another embodiment, the maximum ultrasound intensity that can be safely applied to the tissue or organ is about 2,500 watts/m$^2$. In yet another embodiment, the maximum ultrasound intensity that can be safely applied to the tissue or organ is about 2,000 watts/m$^2$. In yet another embodiment, the maximum ultrasound intensity that can be safely applied to the tissue or organ is about 1,000 watts/m$^2$.

In one embodiment, the maximum ultrasound frequency that can be safely applied to the tissue or organ is about 20 MHz. In another embodiment, the maximum ultrasound frequency that can be safely applied to the tissue or organ is about 15 MHz. In yet another embodiment, the maximum ultrasound frequency that can be safely applied to the tissue or organ is about 10 MHz. In yet another embodiment, the maximum ultrasound frequency that can be safely applied to the tissue or organ is about 7.5 MHz.

Localized release of drugs from the construct of the invention may be achieved by localized application of ultrasound of appropriate intensity and frequency. Microcapsules containing drugs should be resistant to rupture and inadvertent drug release by normal physiological pressures or by ultrasound conditions of the beam passing through tissues not at the target region. Normal physiological pressures refer to those pressures encountered in vivo, including pressures within the heart and arteries, as well as compressive pressures of passing through constrictions, such as capillaries. At minimum, in the use of microbubbles within the circulatory system, the microbubbles within the microcapsules should be resistant to normal intracardiac pressures. The size of the microbubble shell depends in part on the mechanical properties required for the particular drug delivery. Typically, for most vascular applications, populations of microbubbles are in the range from about 25 nm to about 1000 nm. In one embodiment, the diameter of the microbubble ranges from about 0.2 μm to about 4 μm. In another embodiment, the diameter of the microcapsule ranges from about 0.5 μm to about 5 μm. In addition, for many drug delivery applications, it is important that the microcapsules circulate through the capillary network unimpeded. In such instances, microcapsule diameters are in the range of 0.5 to 10 μm.

Induction of leakage of drug-carrying microcapsules may be achieved using ultrasound scanning devices and employing transducers commonly utilized in diagnostic contrast imaging. In such instances, a single ultrasound transducer would be employed for both imaging microcapsules and inducing leakage of microcapsules. The transducer would focus the beam upon the target site and alternately operate at low and high power levels as required by the application.

Another option is to utilize a plurality of transducers focused at the region so that the additive wave superposition at the point of convergence creates a local intensity sufficient to induce leakage of the microcapsules. A separate imaging transducer would be used to image the region for treatment.

A specially designed transducer or multiple transducer set may be incorporated into a wearable object to treat a selected region or organ to alleviate the need for manual placement of the transducer and to facilitate concentration of the ultrasound at the target site.

The transducer may also be incorporated into the distal section of a cannula; or be implanted within the body near the target site. In the first case, an intravascular ultrasound catheter is used to provide the specific ultrasound energy required to induce leakage of the microcapsules as they pass the catheter. The use of such a system provides for the treatment of target sites downstream from the catheter and in places that standard ultrasound imaging would be impaired, for example in the lungs.

In the case of an implant, the ultrasound transducer is surgically implanted within the body at or near the target site for treatment. The transducer may be controlled by induction means through the body wall such that it is inert at all times except during use. The drug-containing microcapsules are injected into the body intravascularly and the transducer energized to induce leakage of the microcapsules at the target site. Such method is useful for longer term or chronic treatment.

To monitor the location of the drug-carrying microcapsules, one or several pulses of sound may be used and the machine may be paused between pulses to receive the reflected sonic signals. In the inducing leakage of the microcapsules, a distinct ultrasound pulse is received, which can be used to calculate the number of microcapsules releasing drug and the cumulative microcapsules triggered.

The drug-containing microcapsules may be imaged with ultrasound under clinically accepted diagnostic power levels for subject safety. While not required, it is preferred that the microcapsules release drug at threshold power levels below the clinically accepted power levels for diagnosis. Specific matching of ultrasound conditions and microcapsule response to such conditions are important factors in achieving such controlled release conditions. Preferred acoustic threshold conditions for leakage are those at a power, frequency, and waveform sufficient to provide a mechanical index from about 0.1 to about 1.9.

The sound energy may be pulsed, but continuous wave ultrasound energy is preferred for maximal triggering of drug release from the microcapsules. If pulsing is employed, sound will preferably be pulsed in echo trained links of at least about 3 wave periods and preferably be pulsed in echo trained links of at least about 5 wave periods at a time.

Either fixed frequency or modulated frequency sound may be used. Preferably, the leakage threshold frequency is between 1 MHz and about 20 MHz. More preferably, the leakage threshold frequency is between 1 MHz and about 20 MHz. Focused, frequency modulated, high energy ultrasound may increase the rate of local gas expansion within the microbubbles, allowing for local delivery of therapeutics.

Pharmaceutical Compositions

Compositions comprising a construct of the invention may be formulated and administered to a subject diagnosed with a particular disease or disorder, or thought to be at risk for a particular disease or disorder. In addition, compositions comprising a construct of the invention may be formulated and administered to a subject diagnosed with a disease or disorder for the purpose of treating the disease or disorder.

The invention encompasses the preparation and use of a pharmaceutical composition comprising a construct as described herein, wherein the construct further comprises a compound useful for treatment of a disease or disorder as an active ingredient. Such a pharmaceutical composition may consist of a construct and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

The formulations of the pharmaceutical compositions described herein may be prepared by any method known or hereafter developed in the art of pharmacology. In general, such preparatory methods include the step of bringing a construct comprising an active ingredient into association with a carrier or one or more other accessory ingredients, and then, if necessary or desirable, shaping or packaging the product into a desired single-dose or multi-dose unit.

Although the descriptions of pharmaceutical compositions provided herein are principally directed to pharmaceutical compositions that are suitable for ethical administration to humans, it will be understood by the skilled artisan that such compositions are generally suitable for administration to subjects of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, and mammals including commercially relevant mammals such as cattle, pigs, horses, sheep, cats, and dogs.

Pharmaceutical compositions that are useful in the methods of the invention may be prepared, packaged, or sold in formulations suitable for oral, parenteral, buccal, or another route of administration.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of a non-limiting example, the composition may comprise between 0.1% and 100% (w/w) active ingredient.

In addition to the active ingredient, a pharmaceutical composition of the invention may further comprise one or more additional pharmaceutically active agents.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like, hi particular, parenteral administration is contemplated to include, but is not limited to, subcutaneous, intraperitoneal, intramuscular, intrasternal injection, intravenous, intra-arterial, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, and emulsions in aqueous vehicles. Such formulations may further comprise one or more additional ingredients including, but not limited to, suspending, stabilizing, or dispersing agents. The formulations may comprise oil and/or detergent components, as long as these oil and/or detergent components do not disrupt or destabilize the construct of the invention. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition. In another embodiment, the formulation for a long-lasting imaging agent using the construct of the invention has lower oil content that a formulation for a controlled drug delivery agent using the construct of the invention.

The pharmaceutical compositions may be prepared, packaged, or sold in the form of a sterile injectable aqueous suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or diglycerides. Other parentally-administrable formulations that are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

In one embodiment, the drug-carrying microcapsules are introduced intravenously by injection. In another embodiment, the microcapsules are injected intra-arterially. In yet another embodiment, the microcapsules are injected interstitially or directly into any body cavity. A useful dosage of the therapeutic agent will be administered and the mode of administration will vary depending upon the age and weight of the subject and upon the particular therapeutic application intended. Typically, the dosage is initiated at a lower level and increased until the desired therapeutic affect is achieved.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous suspension, an aqueous solution, or an emulsion.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous vehicle. Aqueous vehicles include, for example, water and isotonic saline. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents include, for example, beeswax, hard paraffin, and cetyl alcohol.

Liquid solutions of the active ingredient in aqueous solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline.

Powdered and granular formulations of a pharmaceutical preparation of the invention may be prepared using known methods. Such formulations may be administered directly to a subject, used, for example, to form tablets, to fill capsules, or to prepare an aqueous suspension or solution by addition of an aqueous vehicle thereto. Each of these formulations may further comprise one or more of dispersing or wetting agent, a suspending agent, and a preservative. Additional excipients, such as fillers and sweetening, flavoring, or coloring agents, may also be included in these formulations.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity (as an inhalable mist, for example). Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken, for example, by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other ophthalmologically-administrable formulations which are useful include those which comprise the active ingredient in microcrystalline form or in a liposomal preparation.

The compound may be administered to a subject, preferably a mammal, more preferably a human, as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, and the type and age of the subject.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, and atmospheric conditions, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods

Poly(L-lactic Acid) (PLA) and Polyvinyl alcohol (PVA) were supplied by MP Biomedical (Solon, Ohio). The PLA polymer is reported to have a FW of 100,000, and an inherent viscosity of 1.61 dL/g. The PVA polymer is reported to have a FW of 15,000 and is 88% hydrolyzed.

The lipid 1,2-distearoyl-sn-glycero-3-phosphocholine (DSPC) and the functionalized lipid 1,2-disteroyl-sn-glycero-3-phosphoethanolatnine-N-[methoxy-(polyethyleneglycol)-2000] (mPEG 2000 DPPE) were purchased from Avanti Polar Lipids (Alabaster, Ala.).

Sulfur hexafluoride ($SF_6$) was purchased from Airgas (Allentown, Pa.). All other reagents used were of analytical grade.

Example 1

Cavitation Detection System

Figure 2B:
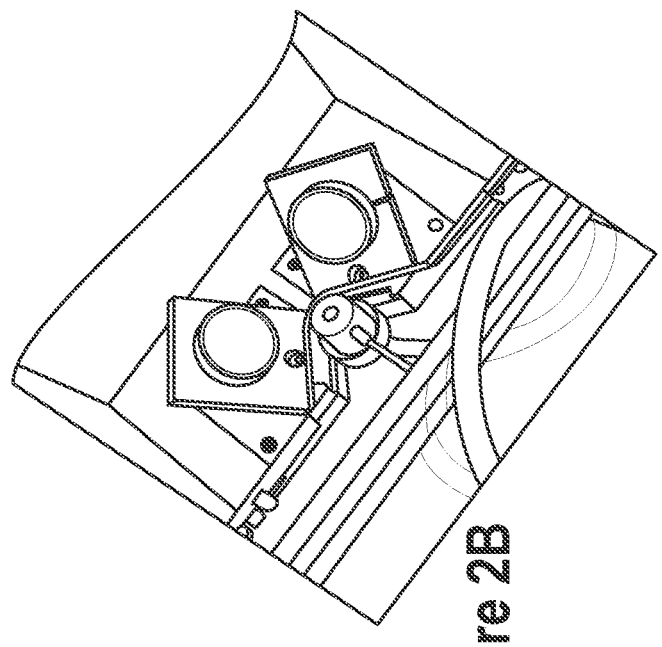
FIGS. 2A-2C illustrate a cavitation detection system. The cavitation detection system is illustrated schematically in FIG. 2A and pictorially in FIG. 2B.
Figure 2A:
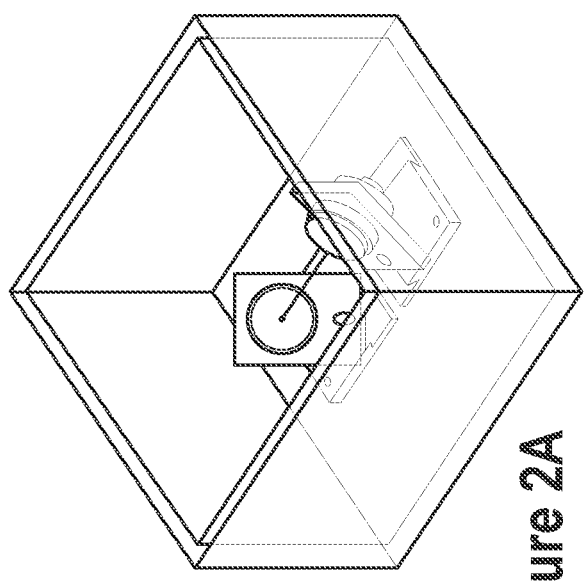
Figure 2C:
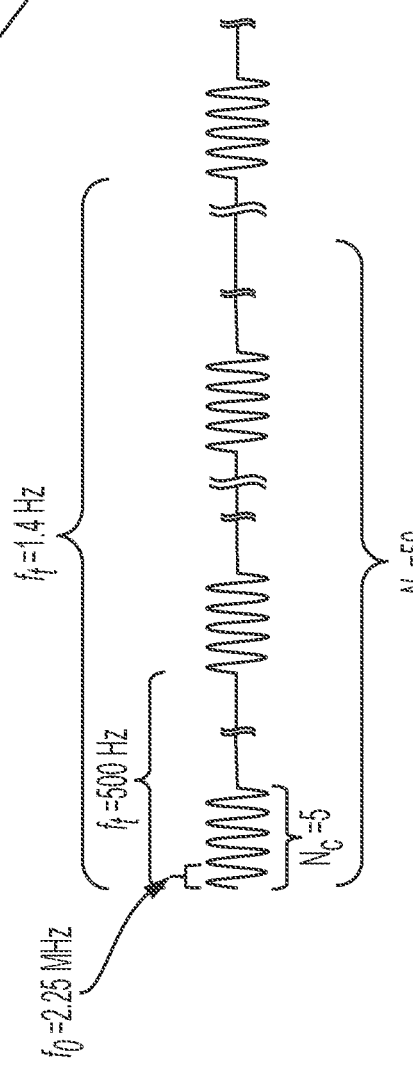

A custom passive cavitation system was designed and built, based on known protocols (Cramer et al., 1982, Appl. Sci. Res. 38:209-14; Hallow et al., 2006, Ultrasound Med. Biol. 32:1111-22; Ammi et al., 2006, IEEE Trans Ultrasonics Ferroelectrics Freq. Control 53:126-36). FIGS. 2A-2C provide a schematic drawing of the physical layout of the system. Two Olympus-NDT (Waltham, Mass.) V395 focused ultrasound transducers, each with a 2.25 MHz center frequency, were oriented at exactly 90° relative to one another within a Plexiglas, de-ionized water-filled tank. One transducer acted as an excitation source and transmitted pulsed ultrasound at a single frequency. A second transducer served as an emission detector and operated over a wide range of frequencies (so that it could detect harmonics, sub-harmonics, and broadband noise). As with the microbubble imaging system, the container was outfitted to house a light source and microscope so as to allow simultaneous optical and acoustic imaging. Raw acoustic data was used to generate acoustic spectrograms, and inertial cavitation events were detected as a sudden appearance of broadband noise.

The region of focal overlap between transducers was ~1 $mm^3$, and the microbubble concentration within the detection system was diluted until no more than one microbubble was observed within the focal region at any given time (which required that in some cases no microbubble was observed). While within the focal region, a microbubble experienced multiple excitation pulses, and microbubble response to each pulse was measured and recorded. Hundreds of microbubbles were sampled in this same manner at a given power setting, and the power was then adjusted and the process repeated so as to determine microbubble response over a range of acoustic intensities.

Microbubble excitation was achieved in two different ways so as to give two versions of the detection system shown in FIGS. 2A-2C. In the first version, the system was operated so as to generate acoustic spectrograms. Ultrasound excitation consisted of a 10 cycle pulse with a center frequency of $f_0$=1.8 MHz. The insonification pulses were generated by a programmable pulser/receiver system (Inoson PCM 100, Inoson GmbH, St. Ingbert, Germany). The pulser/receiver operated in transmission mode, and the spectrum of each scattered signal was determined and plotted as a spectrogram.

Figure 3A:
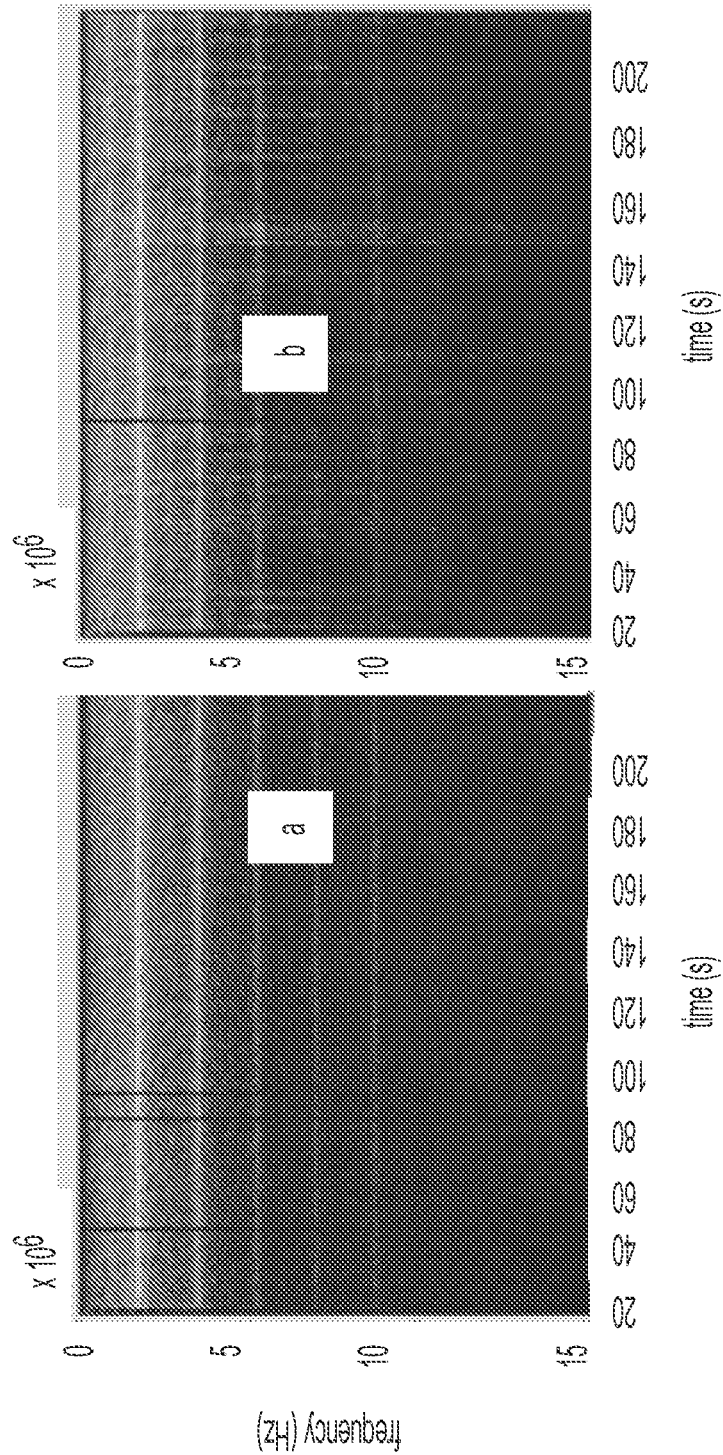
FIGS. 3A-3B illustrate acoustic spectrograms for cavitation detection.
Figure 3B:
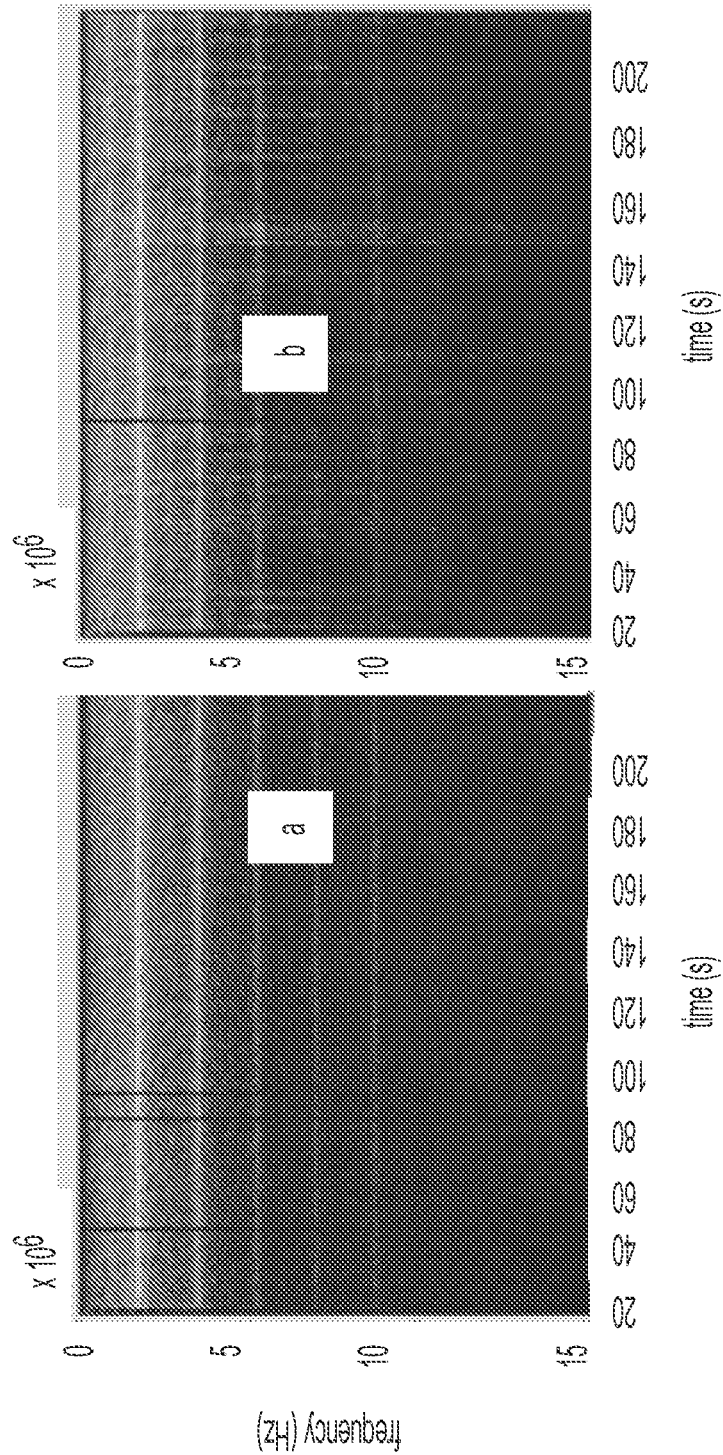

Acoustic spectrograms are appealing in that they provide dramatic visual evidence—or lack thereof—of inertial cavitation at any particular acoustic intensity. FIGS. 3A-3B depict an example.

The horizontal axis in FIGS. 3A-3B tracks results of individual microbubbles as an experiment proceeds in time; each interval in time may be thought of as a repetition of identical experimental conditions, each with a new test microbubble. The ordinate is frequency of scattered acoustic radiation, measured at the detection transducer; the intensity of radiation is given on a relative grey scale (white being highest and black being lowest). Accordingly, there were sporadic cases where one observes vertical black stripes; this indicated that no microbubble was present.

FIG. 3A depicts an acoustic spectrogram obtained at a relatively low transmission intensity (~50 kPa), one for which inertial cavitation did not occur. In this instance, re-radiation of the primary incident wave was observed at 1.8 MHz, evidenced by a bright and horizontal white stripe on the spectrogram. Similarly, horizontal, white stripes were observed parallel to, and at integer multiples of, the primary frequency. These harmonics were indicative of non-linear microbubble oscillations, or stable cavitation, and (to a lesser extent) non-linear propagation of the ultrasound field in water.

The features just mentioned are also prominent in FIG. 3B, which shows an acoustic spectrogram obtained at the highest transmission intensity tested (~1 MPa), and one for which inertial cavitation is believed to have occurred. A horizontal, white stripe (albeit faint) was noticed at 0.9 MHz, exactly half of the primary frequency. This sub-harmonic is evidence that inertial cavitation was present. However, for reasons mentioned previously, a sub-harmonic is not proof of inertial cavitation. The appearance, sporadically throughout the spectrogram, of vertical, white stripes was also observed. These constitute broadband noise, and are direct evidence of inertial cavitation. Quite literally, a new tune was sung after each microbubble cavitates or "pops."

Acoustic spectrograms provide dramatic visual evidence, or lack thereof, of inertial cavitation at any particular acoustic intensity. However, they may not be the preferred tool to examine a wide range of intensities simultaneously. Accordingly, a second version of the cavitation detection system was achieved by using an arbitrary waveform generator (Agilent 33250 A, Agilent Technologies Inc., Santa Clara, Calif.) to transmit a 5-cycle sine burst with a center frequency of $f_0=2.25$ MHz. Another arbitrary waveform generator (Agilent 33120 A, Agilent Technologies Inc., Santa Clara, Calif.) was used to enable a triggering of 50 bursts with a repetition frequency of 250 Hz.

The repetition frequency of the pulse trains was 1.4 Hz (FIGS. 2A-2C). Scattered signals were amplified using an Olympus-NOT 591OR pulser/receiver operated in passive mode. The amplified signals were recorded for further off-line processing using an Acqiris DP-310 digitizer card. A matched filter, set-up for the detection of a five-cycle sine burst at $f_0=2.25$ MHz, was used to detect whether a microbubble was present in the acoustical focus. If detection failed for the following burst, the microbubble was counted as destroyed. Otherwise, it was counted as survived.

Example 2

Synthesis of Microbubbles

In a preferred embodiment, microbubbles were prepared according to the following method. A lipid film containing 10 mg DSPC and 5 mg mPEG 2000 DPPE was deposited onto a scintillating vial from stock solutions dissolved in chloroform, by $N_2$ spin drying followed by 2 hours in vacuum. The dried film was then rehydrated with 4 ml of aqueous phosphate buffered saline (PBS) solution (pH 7) by sonicating the sample (Hielscher UP200S Ultrasonic Processor) for approximately 5 minutes at 33% amplitude. This protocol had the dual effect of dissolving the lipid mixture in solution and raising the temperature above that of the lipid's gel phase transition temperature, 55° C.

The rehydrated solution was then aliquoted out into 2 ml serum vials and sealed. The head space air was evacuated from the vial and replaced with the heavy gas, $SF_6$. Finally the vials were vigorously shaken using the Vialmix shaker (Lantheus Medical Imaging) in order to disperse the gas phase. The resultant microbubbles were allowed to settle at room temperature for 30 minutes. Long term storage was performed at 4° C. A variant of this technique for creating fluorescent microbubbles involved adding 0.15 mg Dil-C16 (1,1'-dihexadecyl-3,3,3',3'-tetramethylindocarbocyanine perchlorate) to the initial lipid film mixture. These techniques successfully produced stable microbubbles with a 1 2 μm diameter.

Example 3

Synthesis of Microcapsules

PLA microcapsules were prepared using the well characterized water/oil/water (W/O/W) emulsion technique described by Freytag and co-workers (J. Controlled Release 2000, 69:197-207) and modified for effectiveness.

In a non-limiting example, a solution of 0.1 ml of microbubbles suspended in PBS plus 0.1 ml 70 mM calcein buffer (internal water phase, W1) was added to 2 ml of 10 mg/ml PLA with 1 weight % extra virgin olive oil (Bertolli) in dichloromethane (intermediate organic phase, O). This solution was then homogenized with the Polytron PT3100 homogenizer for 1 minute at 15,000 rpm in order to create the primary W/O emulsion. Quickly, 16 ml of 2% PVA in water was added to the solution and homogenized at 15,000 rpm for 2 minutes, to generate the double emulsion W/O/W and the outer aqueous phase, W2•

After homogenization, an additional 32 ml of the 2% PVA was added and the mixture was moved to a 400 rpm magnetic stir plate to allow the dichloromethane to evaporate for 24 hours. After drying, the solution was optionally further washed by centrifuging the sample at 15,000×g for 20 minutes. The supernatant PVA solution was siphoned off and replaced with PBS. This technique created stable microcapsules of diameters between 5-10 μm.

Example 4

Characterization of the Construct of the Invention

Figure 1B:
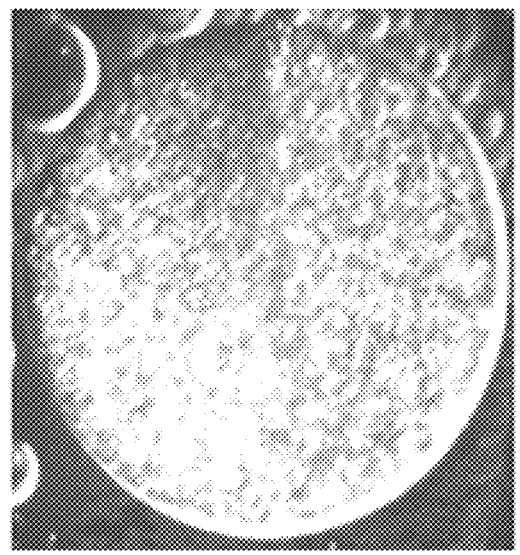
Figures 4A, 4B:
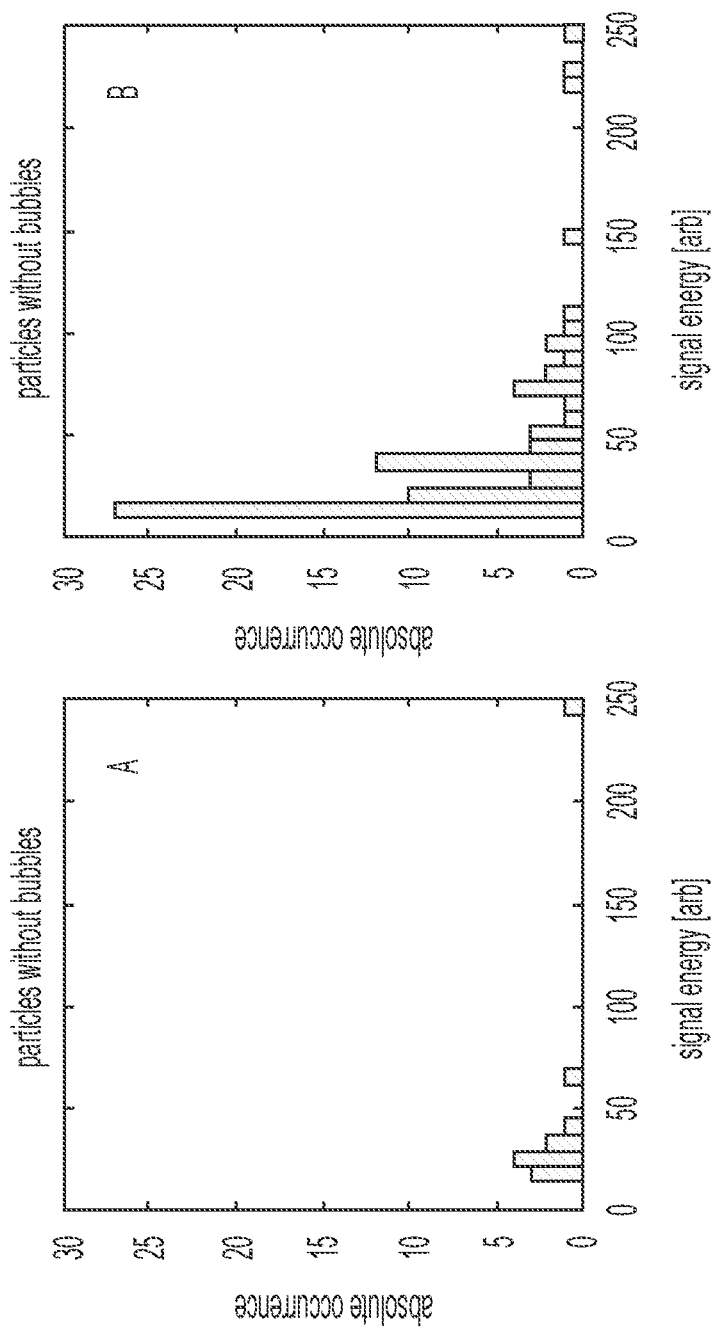
FIGS. 4A-4B illustrate the observation that encapsulation of microbubbles within microcapsules makes microcapsules acoustically active. Histograms of overall signal energy from scattered waveforms of poly(lactic) acid microcapsules without (FIG. 4A) and with (FIG. 4B) encapsulated microbubbles. Ultrasound frequency was 2.25 MHz; pressure was constant.

FIGS. 1A-1B illustrate that encapsulation of microbubbles within microcapsules makes the microcapsules acoustically active. For each experiment, the sample chamber was insonified with a constant pressure, and scattered waveforms were recorded. The signal energy of each waveform was computed, and a histogram over all recorded signal energies is illustrated. Waveforms having an energy close to that of measurement noise were discarded. Microcapsules without bubbles yielded few valid scattering events, whereas microcapsules with encapsulated microbubbles showed significant scattering. FIGS. 5A-5C confirm the result of FIGS. 4A-4B, providing visual evidence of the ultrasound contrast imaging capability of the new vehicle with encapsulated microbubbles. The encapsulated microbubbles observed in FIGS. 5A-5C did not dissolve even in the presence of a sound field, whereas identical, but non-encapsulated, micro bubbles disappeared within several minutes.

In addition to this superior longevity for ultrasound contrast imaging, the construct of the invention also afforded ultrasound activated drug release (FIGS. 6A-6D). The constructs of the invention are shown under visible light microscopy (FIG. 6A), where encapsulated microbubbles are clearly seen in the core of the microcapsules, and fluorescence microscopy (FIG. 6C), which revealed the presence of calcein in the core, FIG. 6B illustrates a light microscope image of calcein-containing microcapsules (without encapsulated microbubbles) after one minute of exposure to ultrasound. FIG. 6D illustrates the same microcapsules of FIG. 6B under fluorescence conditions, revealing the release of calcein into the surrounding aqueous medium. The extent of drug release depends on several factors, such as the ultrasound frequency used. In fact, ultrasound-triggered release from polymeric microcapsules, liposomes, and polymersomes is feasible—even without microbubbles—at a frequency of 20 kHz (for example, FIGS. 6B-6D). Safer and more clinically relevant, however, are the higher ultrasound frequencies used for imaging (1-10 MHz). However, cavitation at the clinical frequencies requires significantly higher pressures than at the lower kHz range. For the purpose of this work, the higher pressures necessary for cavitation were achieved using a custom-built pulser that is more tunable and capable of delivering more power than a standard power amplifier. The new pulser was built according to a similar device described previously [Mleczko & Schmitz, 2008, Proc. IEEE Int Ultrason. Symp., 1686-1689].

Figure 9:
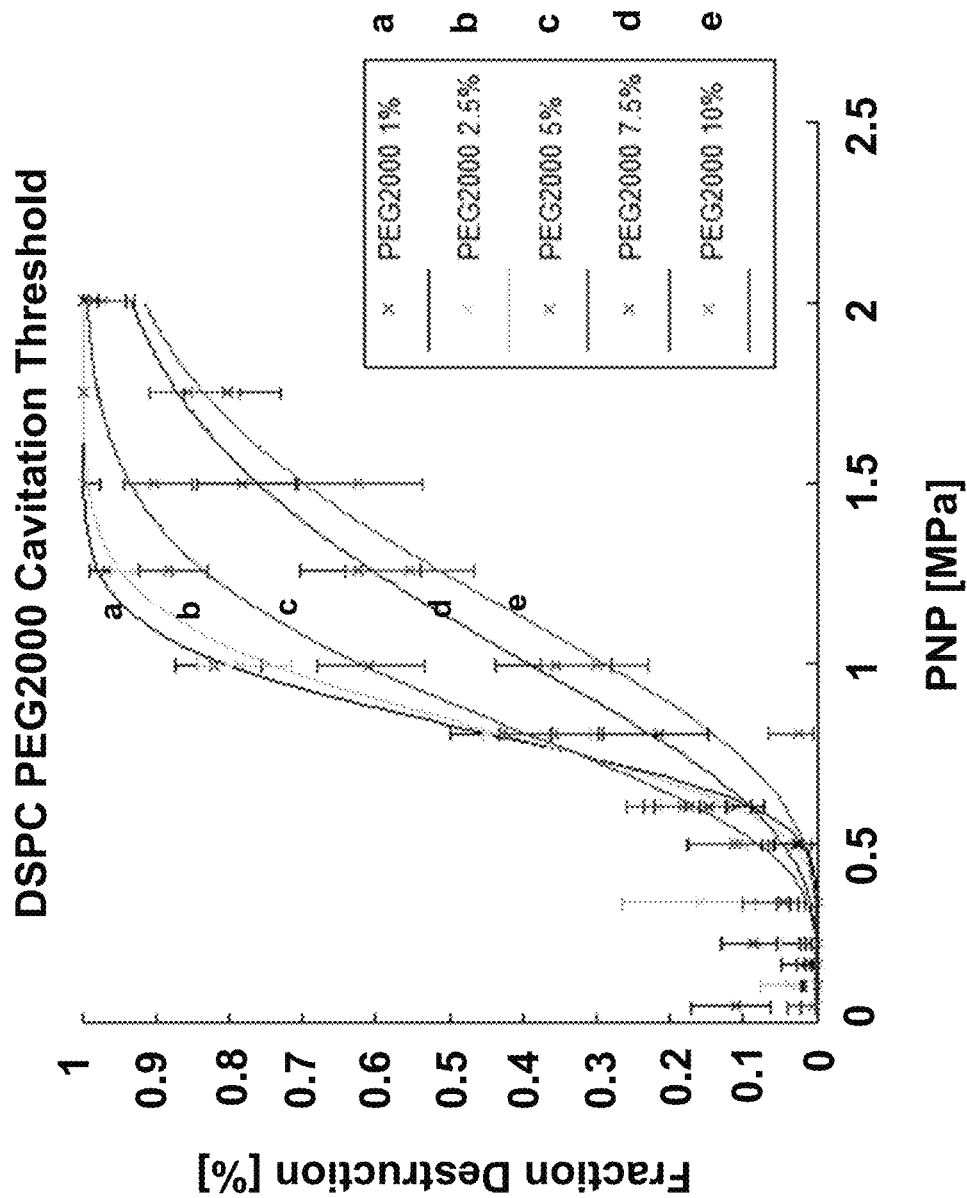
FIG. 9 illustrates the influence of monolayer chemistry on cavitation threshold. The percentage of microbubbles destroyed due to inertial cavitation was plotted as a function of acoustic pressure for PEG 2000, at a range of PEG mole fractions. Both the cavitation threshold, which appears as a discontinuity on the abscissa, and the fraction of bubbles destroyed, which takes on a sigmoidal profile with pressure, were sensitive to changes in PEG mole fraction.

The use of clinical frequencies also motivates the use of microcapsules. Not only do the microbubbles within the microcapsules provide the acoustic activity necessary for enhanced ultrasound contrast during imaging, they also facilitate cavitation at lower pressures than would be required for cavitation of residual, dissolved gases or the solvent itself. This is because the microbubble resonance frequency more closely matches the ultrasound driving frequency. Given that resonance frequency is a function of monolayer bending elasticity and thickness, the use of encapsulated microbubbles offers the advantage that the extent of cavitation may be controlled simply by changing monolayer chemistry. For example, fine tuning of the cavitation threshold may be easily achieved by changing the PEG mole fraction or molecular weight in the microcapsule shell (FIG. 9). Such changes in microbubble cavitation threshold via changes in PEG composition or molecular weight are a means of influencing the microcapsule leakage threshold (FIG. 15).

Example 5

Leakage of Microcapsules

The microcapsules with encapsulated microbubble solution in PBS and 70 mM calcein buffer could be actively leaked by ultrasound. In a non-limiting example, the microcapsules were effectively leaked by ensonifying them at 2.25 MHz with a 4 cycle pulse at a pulse repetition frequency of 5 Hz with bursts of 300 pulses. The amplitude of the electrical input wave was 50 V. 3-ml samples are taken every minute for 5 minutes in order to quantify their calcein leakage in a fluorescence spectrometer (PTI, Birmingham N.J.). As per the fluorescent properties of calcein, the samples were excited at 475 nm, and the scan read for emissions between 490-540 nm. An additional control sample of microcapsules with encapsulated microbubbles was left without sonication. For this control sample, leakage was a result of passive diffusion and allowed normalization of the results.

Figure 7:
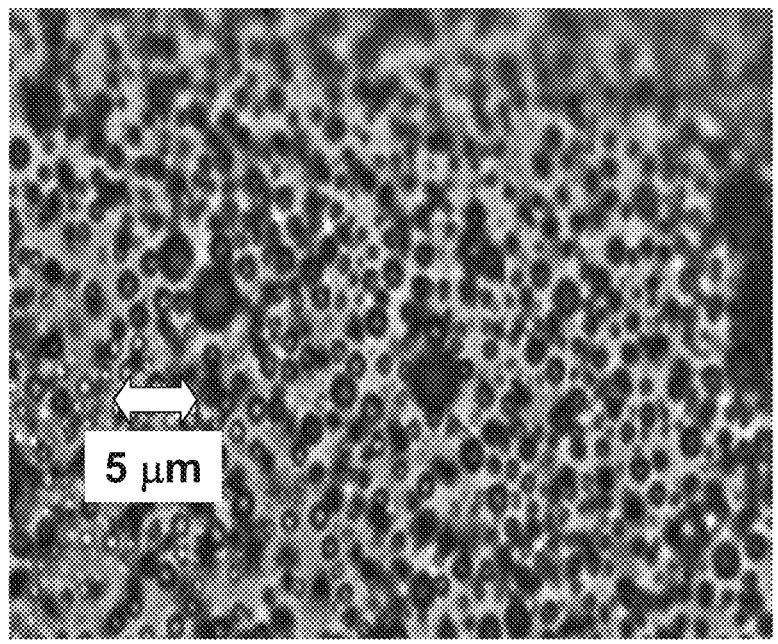
FIG. 7 illustrates a non-limiting batch of microbubbles, wherein the microbubbles comprise an SF6 core and a shell of 95 mole % DSPC plus 5 mole % PEG6000MS. DSPC concentration is 2 mg/mL in the original formulation, which yields on the order of $10^9$ microbubbles per mL.

FIG. 7 illustrates a batch of microbubbles. The particular microbubbles shown were prepared by the method of sonication with live gas sparging (the gas used in this case was sulfur hexafluoride, SF6, and the stabilizing shell was the phospholipid distearoylphosphatidylcholine, DSPC). A preferred method involves head-space gas exchange and shaking, rather than sonication, to create the microbubbles. The latter method gives microbubbles that are more monodisperse and stable against gas dissolution for many months.

Bubbles and GUVs were observed with a custom system (Postema et al., 2006, Biomed. Tech. 51(Suppl.):V75-76; Postema et al., 2006, Proc. IEEE int. ultrason. symp. 1564-67; Mleczko et al., 2006, Proc. IEEE int. ultrason. Symp. 1369-72). In this set-up, samples were inserted via syringe into a 200 μm inner diameter (8 μm wall thickness) CUPROPHAN® RCSS cellulose capillary (Membrana GmbH, Wuppertal, Germany) that was isolated within a de-ionized water-filled Perspex tank, illuminated from below with a DC 421 40,000 footcandle fiber optic continuous light source (Stockeryale. Inc., Salem, N.H.), and observed from above through a LUMPlan FL 60× high numerical aperature (NA=0.90) water immersion objective lens (Olympus Deutschland GmbH, Hamburg, Germany). The Perspex container itself was mounted on top of a custom-built micron-adjustable x.-y table, and the microscope was connected to a video camera. A spherically focused, 2.25 MHz (Panametrics. Inc., Waltham, Mass.) transducer was oriented perpendicular to the capillary and at 90° relative to both the light source and the microscope objective. The configuration was such that optical focal and acoustic focal regions overlapped, and the capillary was positioned within the region of overlap.

Example 6

Transducer Operation: Mechanism of Microcapsule Membrane Rupture

The leakage profiles measured in Example 5 are a result of stable cavitation or inertial cavitation, or both. Constructs are prepared with varying proximity of the microbubbles to microcapsule shell (in the range of 0.1 to 10 microbubble diameters). The constructs are subjected to a range of acoustic pressures that encompasses the inertial cavitation threshold of the microbubbles encapsulated within the construct. Multiple aliquots of each construct are made, and only one aliquot of a given construct is subjected to a given pressure. This is because each aliquot of each construct type is encapsulated with calcein, used here to check for the mere presence of leakage. In this way) a second threshold is identified, namely the pressure at which leakage is achieved. If this threshold matches the inertial cavitation threshold, then this will point to inertial cavitation—and the shock waves it produces—as a leakage mechanism. If, on the other hand, the leakage threshold is lower than the inertial cavitation threshold, then this will point to stable cavitation—and associated shear stresses due to microstreaming that stable cavitation induces—as leakage mechanism. Leakage across the microcapsule shell might also involve mechanisms that do not involve microbubble cavitation.

Example 7

Long Lasting Ultrasound Contrast Imaging

Figure 10:
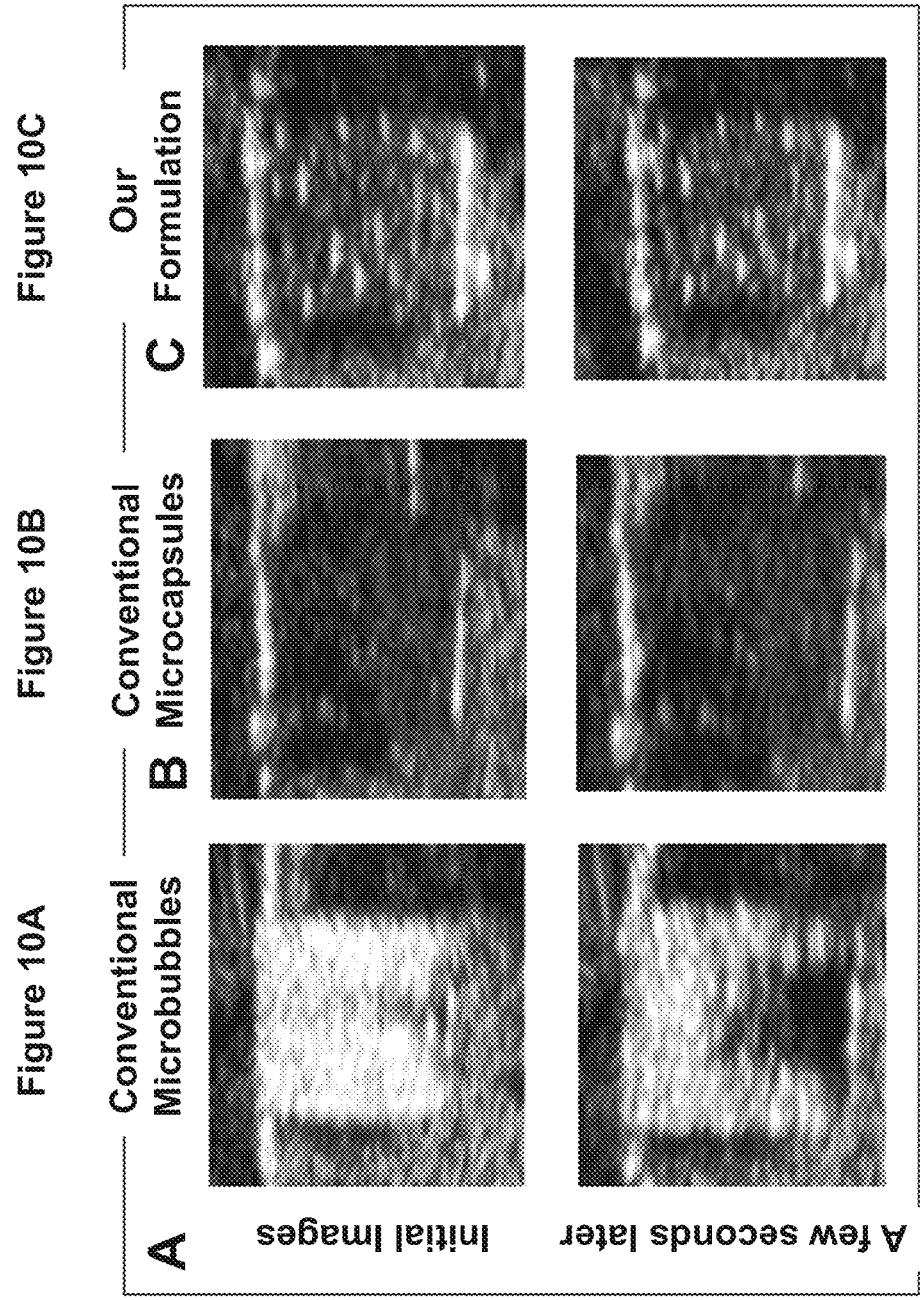
FIGS. 10A-10C illustrate the ultrasound images of three samples: conventional phospholipid-coated microbubbles (FIG. 10A), conventional PLA microcapsules (FIG. 10B) and the construct comprising PLA microcapsules with phospholipid coated microcapsules contained within the aqueous core (FIG. 10C).

FIGS. 10A-10C illustrate the superior longevity of the construct of the invention relative to traditional phospholipid-coated microbubbles. Ultrasound images of three samples (conventional microbubbles, empty conventional microcapsules, and the construct of the invention) are illustrated immediately after applying ultrasound (top row) and after a few seconds of applied ultrasound (bottom row). The conventional microcapsules (middle column) did not exhibit any appreciable brightness (which would stem from microbubble acoustic activity) because they did not contain microbubbles. The construct of the invention were distinct from conventional microbubbles (left column). The individual microbubbles in the construct of the invention were as bright as the individual conventional microbubbles; the conventional microbubbles appeared to be more plentiful because the concentration of conventional microbubbles used was much higher than for the construct of the invention. Interestingly, the conventional microbubbles began to disappear within just a few seconds (FIG. 10A, top v. bottom). The pressure associated with the ultrasound wave caused the gas inside the microbubbles to dissolve in the surrounding bulk aqueous phase. However, there was no discernible change in the brightness of the microbubbles in the construct of the invention (FIG. 10C, top v, bottom). The gas within the microbubbles in the construct of the invention could not dissolve into the bulk aqueous phase due the presence of an impervious microcapsule shell that surrounded the microbubbles and kept them intact within the aqueous core of the microcapsule. The microbubbles in the construct of the invention avoided dissolution at least 600 times (and probably much more) longer than conventional microbubbles.

In a separate test, the construct of the invention persisted for as long as 30 minutes at an external pressure that caused conventional microbubbles to disappear completely within a few seconds (FIG. 13).

Example 8

Ultrasound Triggered Release

Figure 11:
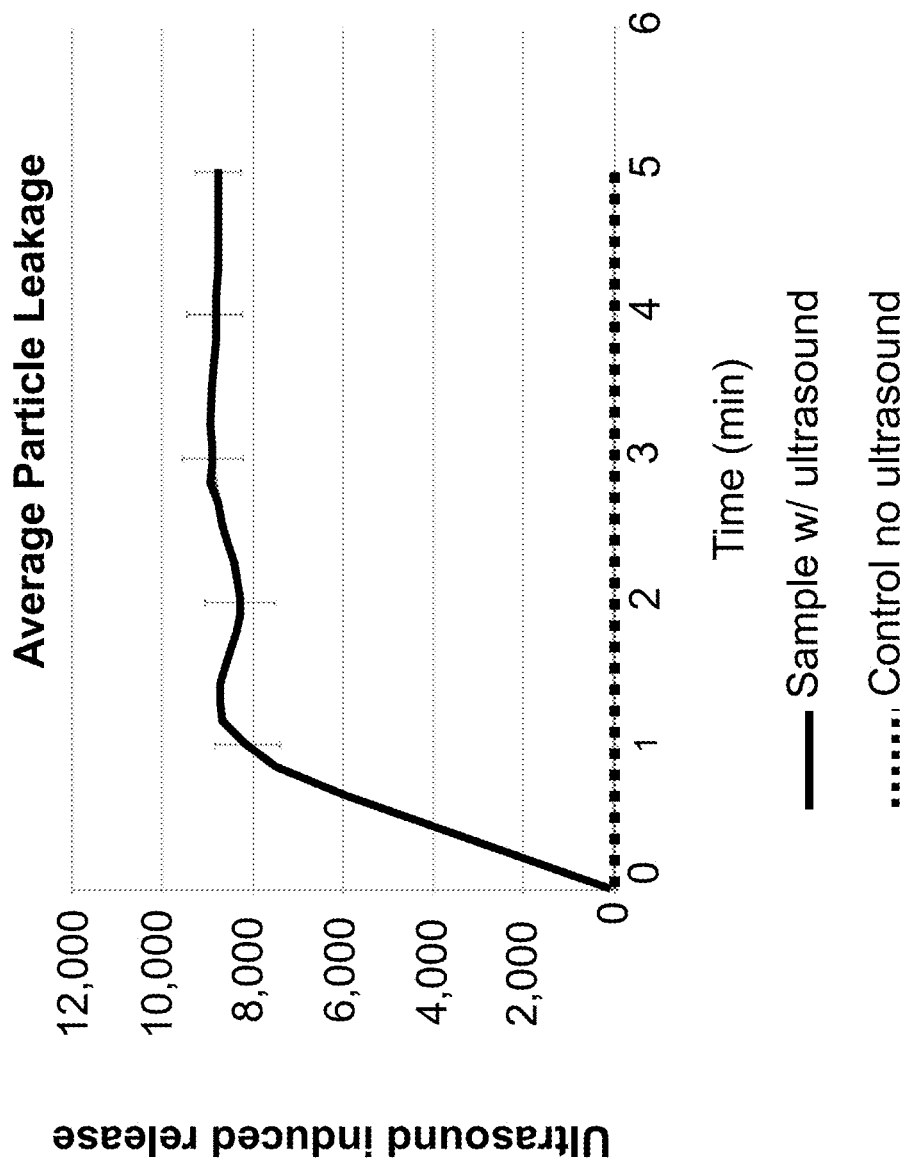
FIG. 11 illustrates controlled drug release using ultrasound as a trigger. Leakage profiles for a construct of the invention in the absence (broken line) and presence (continuous line) of ultrasound are illustrated. Shown are the average of three experiments with error bars (representing one standard deviation). Ultrasound frequency was 2.25 MHz.

FIG. 11 illustrates the ability of the construct of the invention to release drug on command using ultrasound as a remote trigger. In the presence of a high intensity ultrasound pressure wave (over the leakage threshold), the microcapsule shell that surrounds the aqueous core (in which the drug and phospholipid-coated microbubbles are contained) was no longer impervious. Rather, the microcapsule shell was permeable to drug (at least in part owing to diffusion, although destruction or other disruption of the shell and pore formation cannot be ruled out). As a result, drug was released steadily into the surrounding bulk phase (outside the microcapsule).

In FIG. 11, the leakage profiles for the construct of the invention in the absence (broken line) and presence (continuous line) of ultrasound are depicted. In this case, the formulation included calcein, a water-soluble fluorescent dye that mimics a hydrophilic drug. When inside the aqueous core of a microcapsule, calcein did not fluoresce due to self-quenching. Leakage of calcein from a microcapsule into the bulk aqueous phase alleviated self-quenching and enabled calcein to fluoresce.

Ultrasound-induced drug release was thus reported here as leakage of calcein, measured as an increase in calcein fluorescence. In the absence of ultrasound (or at low ultrasound intensities used for imaging), no appreciable leakage was observed. In the presence of ultrasound (2.25 MHz, −0.5 MPa PNP), significant leakage was observed within one minute. Shown are the average of three experiments with error bars (representing one standard deviation).

Example 9

Feasibility of Encapsulation and Subsequent Activation with Ultrasound.

Figure 12A:
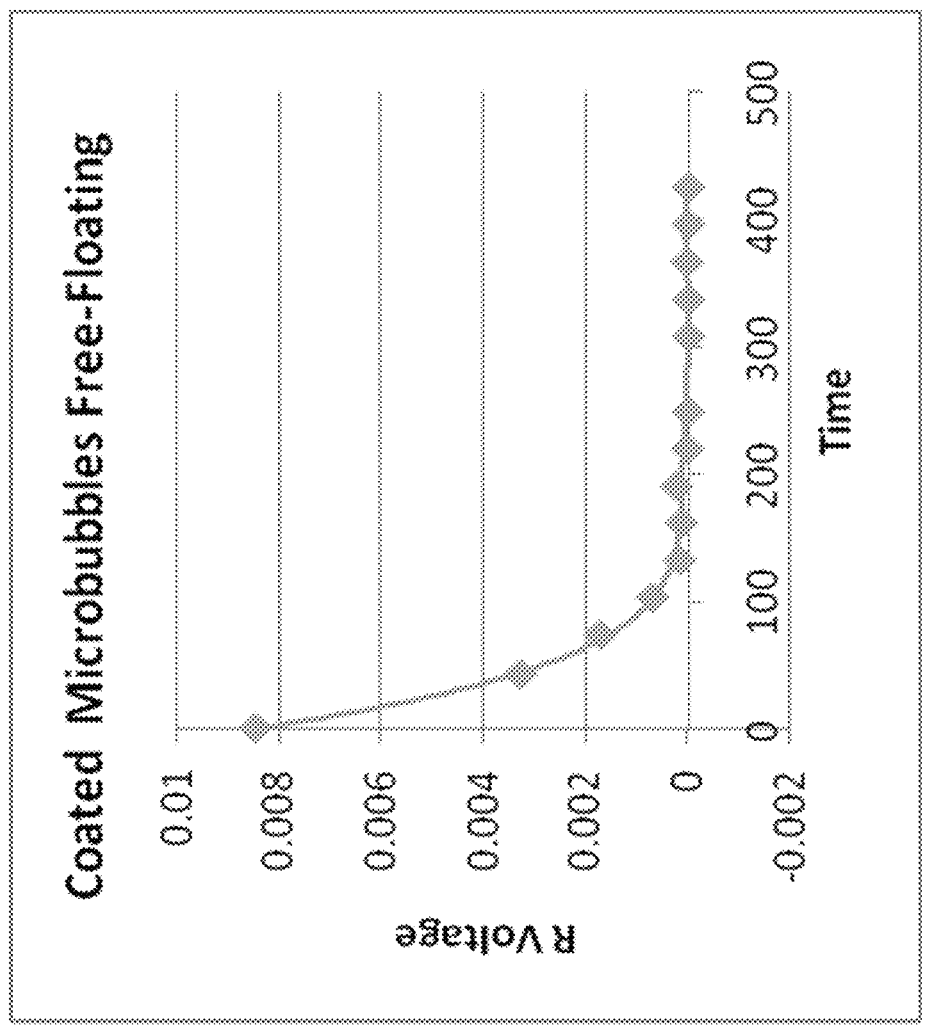
FIGS. 12A-12C illustrates data for a combined phase-inversion/cavitation experiment for free-flowing microbubbles (FIG. 12A), microbubbles encapsulated inside microcapsules (FIG. 12B) and microcapsules without bubbles (FIG. 12C).
Figure 12B:
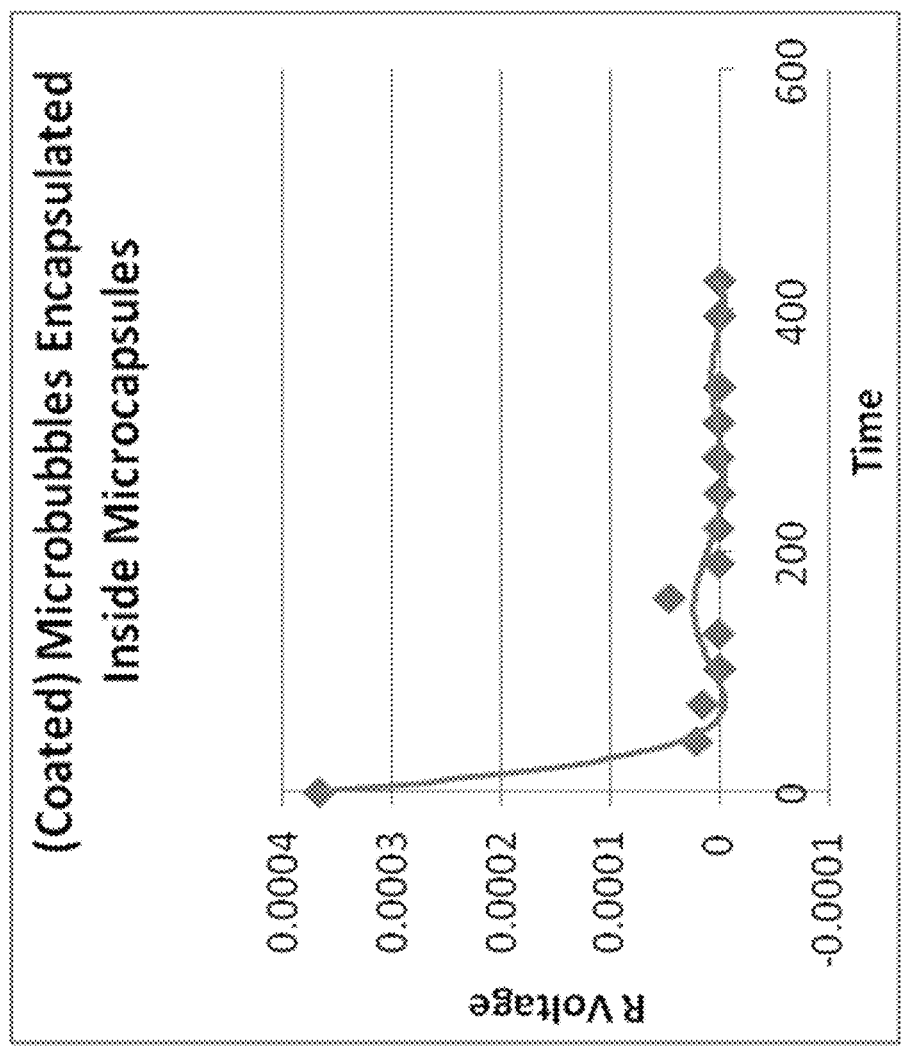
Figure 12C:
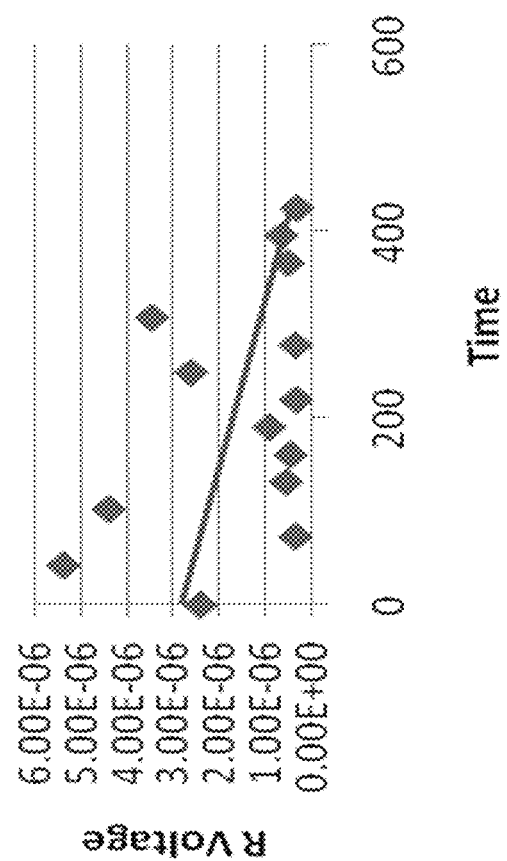
Figure 14:
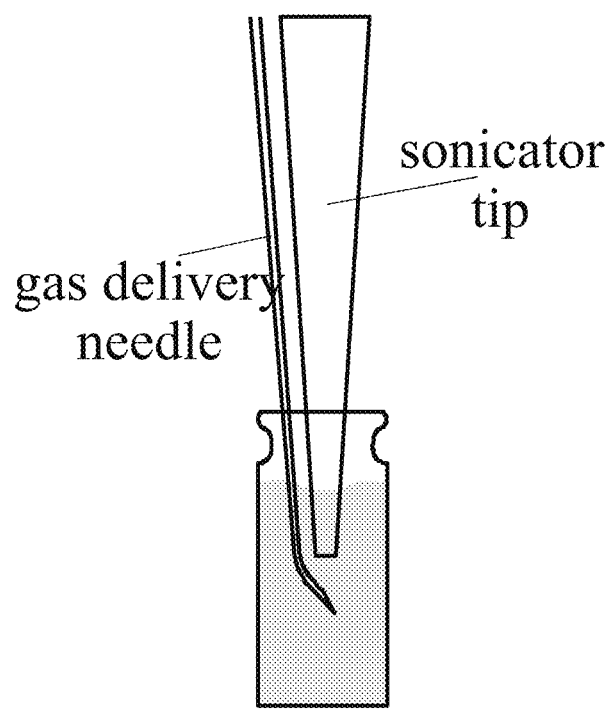
FIG. 14 illustrates a non-limiting method of microbubble synthesis by direct sonication (24 kHz, Hielscher UP400S) while sparging SF6 into an aqueous suspension of phospholipid multi-lamellar microcapsules. Gas is sparged through a syringe needle located directly beneath the tapered sonicator probe.

Illustrated in FIGS. 12A-12C are results of microbubble destruction/activation achieved by cavitation with ultrasound at a frequency of 2.25 MHz. In each of FIGS. 12A-12C, the voltage received at a detector is measured as the sample is excited with 2.25 MHz ultrasound at a peak negative pressure of −2.2 MPa. The amount of signal is proportional to the amount of non-linear response to ultrasound, due to the presence of microbubbles. FIG. 12A illustrates results of microbubbles alone; FIG. 12B illustrates results of microbubbles that have been encapsulated within microcapsules, and FIG. 12C illustrates results of "empty" microcapsules (that is, microcapsules containing no microbubbles), which registers effectively no voltage. As mentioned above, encapsulation means that the coated microbubbles are contained within the aqueous interior of a larger microcapsule. FIG. 12B shows a significant initial signal that was approximately two orders of magnitude higher than the baseline, demonstrating that microbubbles were encapsulated within the microcapsules and that the encapsulated microbubbles oscillate so as to give an acoustic signal that can be used for enhanced ultrasound contrast.

Moreover, the initial signal of the encapsulated sample was an order of magnitude less than that observed for a sample of traditional, unencapsulated microbubbles (FIG. 12A). This is consistent with only a fraction of the microbubbles being encapsulated and any unencapsulated microbubbles being removed from the sample, thereby giving a much lower overall microbubble concentration in the experiment. Both FIGS. 12A and 12B showed a sharp reduction in signal with time, due to microbubble destruction by inertial cavitation. No such destruction was observed in FIG. 12C because there were no microbubbles present to be destroyed. This demonstrates that microbubbles may be controllably activated, even though they are encapsulated within the microcapsules. This method of microbubble activation facilitates leakage of the contents from the microcapsule.

Taken together, these results demonstrate three key facts: 1) (coated) microbubbles may be encapsulated within microcapsules, 2) encapsulated microbubbles are acoustically active, and 3) encapsulated microbubbles may be activated and cause leakage of the microcapsule upon command using high-frequency ultrasound as a remote trigger.

Example 10

Feasibility of Enhanced Longevity Due to Encapsulation.

High ultrasound pressures would be useful in drug delivery (or other therapeutic agent) application but not for imaging. When a lower pressure that falls below the leakage threshold (as would be the case for imaging) is used, a much different result may be obtained. When pressure is applied but inertial cavitation does not take place, traditional microbubbles would disappear due to dissolution in the surrounding aqueous medium. Encapsulated microbubbles, on the other hand, do not dissolve even under applied pressure. The invention includes a construct that facilitates ultrasound-induced delivery of a therapeutic agent and that serves as an enhanced ultrasound contrast agent that avoids ultrasound-induced dissolution in aqueous fluids.

The micrographs in FIG. 13 illustrate two samples (the left column shows a sample of freely floating, coated microbubbles, and the right column shows a sample of the invention, which comprises the same coated microbubbles shown in the left column encapsulated within a microcapsule) at various points in time. At the initial time a pressure of 412 kPa was applied (this pressure was sufficient to enable ultrasound imaging but not sufficient to cause inertial cavitation of microbubbles—the latter being the mechanism to initiate drug release). The top row illustrates initial time; the middle row illustrates after 5 seconds; and the bottom row illustrates after 30 minutes at the applied pressure of 412 kPa. These results demonstrate that encapsulation of microbubbles within microcapsules avoids pressure-induced dissolution that would otherwise arise if the microbubbles were freely floating (as is the ease with conventional contrast agents). Thus, the constructs of the invention are ultrasound contrast agent with enhanced longevity compared with conventional ultrasound contrast agents.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A construct comprising an echogenic microcapsule comprising:
   a contiguous first shell uninterrupted by gas, the shell comprising a self-assembling molecule;
   an aqueous core surrounded by the first shell;
   at least one microbubble encapsulated by a second shell;
      wherein the at least one encapsulated microbubble comprises a gas and is within
      the aqueous core of the echogenic microcapsule; and
   wherein the first shell becomes permeable to the aqueous core when the microcapsule is irradiated with an ultrasound intensity that is equal to or higher than the leakage threshold intensity of the microcapsule.

2. The construct of claim 1, wherein the self-assembling molecule comprises a polymer or phospholipid.

3. The construct of claim 2, wherein the polymer is a di-block copolymer.

4. The construct of claim 2, wherein the first shell comprises a liposome, unilamellar vesicle, or giant unilamellar vesicle (GUV).

5. The construct of claim 1, wherein the first shell further comprises from about 0.001% to about 10% of an oil.

6. The construct of claim 1, wherein a therapeutic agent is in the aqueous core or is dispersed in the first shell.

7. The construct of claim 1, wherein the at least one encapsulated microbubble is free-floating in the aqueous core or is tethered to the inner surface of the microcapsule.

8. The construct of claim 1, wherein the gas comprises a chemical selected from the group consisting of air, octafluoropropane, perfluorobutane, and sulfur hexafluoride.

9. The construct of claim 1, wherein the diameter of the first shell is about 0.5 µm to about 10 µm.

10. The construct of claim 1, wherein the diameter of the first shell is about 0.5 µm to about 5 µm.

11. The construct of claim 1, wherein the diameter of the first shell is about 0.2 µm to about 4 µm.

12. The construct of claim 1, wherein the diameter of the microbubble is about 25 nm to about 1 µm.

13. The construct of claim 1, wherein the diameter of the microbubble is about 0.2 µm to about 4 µm.

14. The construct of claim 1, wherein the second shell comprises a gel-phase lipid.

15. The construct of claim 14, wherein the gel-phase lipid comprises a gel-phase phospholipid.

16. The construct of claim 1, wherein the second shell comprises at least one compound selected from the group consisting of PEGylated phospholipid, DMPC (dimyristoylphosphatidylcholine), DSPC (di stearoylphosphatidylcholine), and egg PC (egg phosphatidylcholine).

17. A construct comprising an echogenic microcapsule comprising:
   a contiguous first shell uninterrupted by gas the shell comprising a self-assembling molecule;
   an aqueous core surrounded by the first shell; and
   at least one microbubble encapsulated by a second shell, wherein the encapsulated microbubble comprises a gas and is within the aqueous core of the echogenic microcapsule;
   wherein the contiguous first shell protects the at least one encapsulated microbubble and yields increased ultrasound longevity relative to an identical microbubble that is not encapsulated by the contiguous first shell; and
   wherein the contiguous first shell is ruptured upon cavitation of the at least one encapsulated microbubble.

18. The construct of claim 17, wherein the self-assembling molecule comprises a polymer or phospholipid.

19. The construct of claim 18, wherein the polymer is a di-block copolymer.

20. The construct of claim 18, wherein the first shell comprises a liposome, unilamellar vesicle, or giant unilamellar vesicle (GUV).

21. The construct of claim 17, wherein the first shell further comprises from about 0.001% to about 10% of an oil.

22. The construct of claim 17, wherein a therapeutic agent is in the aqueous core or is dispersed in the first shell.

23. The construct of claim 17, wherein the at least one encapsulated microbubble is free-floating in the aqueous core or is tethered to the inner surface of the microcapsule.

24. The construct of claim 17, wherein the gas comprises a chemical selected from the group consisting of air, octafluoropropane, perfluorobutane, and sulfur hexafluoride.

25. The construct of claim 17, wherein the diameter of the first shell is about 0.5 µm to about 10 µm.

26. The construct of claim 17, wherein the diameter of the first shell is about 0.5 µm to about 5 µm.

27. The construct of claim 17, wherein the diameter of the first shell is about 0.2 µm to about 4 µm.

28. The construct of claim 17, wherein the diameter of the microbubble is about 25 nm to about 1 µm.

29. The construct of claim 17, wherein the diameter of the microbubble is about 0.2 µm to about 4 µm.

30. The construct of claim 17, wherein the second shell comprises a gel-phase lipid.

31. The construct of claim 30, wherein the gel-phase lipid comprises a gel-phase phospholipid.

32. The construct of claim 17, wherein the second shell comprises at least one compound selected from the group consisting of PEGylated phospholipid, DMPC (dimyristoylphosphatidylcholine), DSPC (di stearoylphosphatidylcholine), and egg PC (egg phosphatidylcholine).

33. The construct of claim 17, wherein the construct can withstand ultrasound contrast imaging at ultrasound intensities below the leakage threshold of the microcapsule.

34. The construct of claim 17, wherein the construct is produced using a water/oil/water emulsion technique.

35. A method of imaging a tissue or an organ in a subject, wherein the method comprises:
   administering to the subject a pharmaceutical composition comprising a construct comprising an echogenic microcapsule comprising:
      a contiguous first shell uninterrupted by gas, the shell comprising a self-assembling molecule;
      an aqueous core surrounded by the first shell;
      at least one microbubble encapsulated by a second shell;
         wherein the at least one encapsulated microbubble comprises a gas and is within the aqueous core of the echogenic microcapsule; and
         wherein the first shell becomes permeable to the aqueous core when the microcapsule is irradiated with an ultrasound intensity that is equal to or higher than the leakage threshold intensity of the microcapsule;
   and,
   monitoring the location of the construct within the subject by ultrasound techniques using a first ultrasound intensity, wherein the first ultrasound intensity is lower than the leakage threshold intensity of the microcapsule.

36. A method of delivering a therapeutic cargo to a tissue or organ in a subject, wherein the method comprises:

administering to the subject a pharmaceutical composition comprising a construct comprising an echogenic microcapsule, wherein a therapeutic cargo is associated with the construct, wherein the echogenic microcapsule comprises:
   a contiguous first shell uninterrupted by gas, the shell comprising a self-assembling molecule;
   an aqueous core surrounded by the first shell;
   at least one microbubble encapsulated by a second shell;
      wherein the at least one encapsulated microbubble comprises a gas and is within the aqueous core of the echogenic microcapsule;
      wherein the first shell becomes permeable to the aqueous core when the microcapsule is irradiated with an ultrasound intensity that is equal to or higher than the leakage threshold intensity of the microcapsule;
monitoring the location of the construct within the subject by ultrasound techniques using a first ultrasound intensity, wherein the first ultrasound intensity is lower than the leakage threshold intensity of the microcapsule;
detecting presence of the construct in the vicinity of the organ or tissue based on ultrasound monitoring; and,
releasing the therapeutic cargo from the construct by applying a second ultrasound intensity to the construct, wherein the second ultrasound intensity is: equal to or higher than the leakage threshold of the microcapsule, and equal to or lower than the maximum ultrasound intensity that can be safely applied to the tissue or organ.

37. A method of treating a disease or disorder in a subject in need thereof, the method comprising:

administering to the subject an effective amount of a pharmaceutical composition comprising a construct comprising an echogenic microcapsule, wherein a therapeutic cargo that treats the disease or disorder is associated with the construct, wherein the echogenic microcapsule comprises:
   a contiguous first shell uninterrupted by gas, the shell comprising a self-assembling molecule;
   an aqueous core surrounded by the first shell;
   at least one microbubble encapsulated by a second shell;
      wherein the at least one encapsulated microbubble comprises a gas and is within the aqueous core of the echogenic microcapsule;
      wherein the first shell becomes permeable to the aqueous core when the microcapsule is irradiated with an ultrasound intensity that is equal to or higher than the leakage threshold intensity of the microcapsule;
monitoring the location of the construct within the subject by ultrasound methods using a first ultrasound intensity, wherein the first ultrasound intensity is lower than the leakage threshold intensity of the microcapsule;
detecting presence of the construct in the vicinity of an organ or tissue that is associated with the disease or disorder, based on ultrasound monitoring; and,
releasing the therapeutic cargo from the construct by applying a second ultrasound intensity to the construct, wherein the second ultrasound intensity is: equal to or higher than the leakage threshold of the microcapsule, and equal to or lower than the maximum ultrasound intensity that can be safely applied to the tissue or organ.

* * * * *